US006667278B2

(12) United States Patent
Back et al.

(10) Patent No.: US 6,667,278 B2
(45) Date of Patent: Dec. 23, 2003

(54) NON-STEROIDAL MIMETICS OF BRASSINOLIDE

(75) Inventors: Thomas G. Back, Calgary (CA); Richard P. Pharis, Calgary (CA); Denise L. Andersen, Vancouver (CA); Gabriel Sung, Wilmington, DE (US)

(73) Assignee: University Technologies International Inc., Calgary (CA)

( * ) Notice: Subject to any disclaimer, the term of this patent is extended or adjusted under 35 U.S.C. 154(b) by 75 days.

(21) Appl. No.: 10/004,442

(22) Filed: Dec. 5, 2001

(65) Prior Publication Data
US 2002/0115570 A1 Aug. 22, 2002

Related U.S. Application Data
(60) Provisional application No. 60/251,039, filed on Dec. 5, 2000.

(51) Int. Cl.[7] .......................... A01N 31/00; C07C 39/12
(52) U.S. Cl. ...................................... 504/354; 568/734
(58) Field of Search .......................... 504/354; 568/734

(56) References Cited

U.S. PATENT DOCUMENTS

| 6,063,731 | A | 5/2000 | Back et al. |
| 6,316,625 | B1 | 11/2001 | Babu et al. |
| 6,319,939 | B1 | 11/2001 | Mabire et al. |

OTHER PUBLICATIONS

Back, et al. "Design Synthesis and Bioactivity of the First Nonsteroidal Mimetics of Bassinolide" Paper, J. Org. Chem. 2001, 66; 7129–7141.
Grove, et al. "Brassinolide, a plant growth–promoting steroid isolated from *Brassica napus* pollen", Article in Nature, vol. 281, Sep. 20, 1979.

Back, "Stereoselective Synthesis of Brassinosteroids" Article in Studies in Natural Products Chemistry, vol. 16, pp. 320–365.
Back, et al "Concise, Improved Procedure for the Synthesis of Brassinolide and Some Novel Side–Chain Analogues" The Journal of Organic Chemistry, vol. 62, No. 4, pp. 1179–1182.
McMorris, et al. "Improved Synthesis of Brassinolide" Department of Chemistry, U of California, Paper, pp. 295–302.
Adam, et al., "New Developments in Brassinosteroid Research" Article in Studies in Natural Products Chemistry, vol. 18, pp 495–549.
Mandava, N. Bhushan, "Plant Growth–Promoting Brassinosteroids", Article in Ann. Rev. Plant Physiol. Plant Mol. Biol. 1988. pp. 23–53.
Adam, et al. "Review Article No. 19 Brassinosteroids"— Psytochemistry vol. 25, No. 8, pp. 1787–1799.
Parish, et al. "Biochemistry and Function of Sterols" Article CRC Press Chapter 15, pp. 201–220.
Brosa, et al. "Brassinosteroids: A New Way to Define the Structural Requirements" Article in Tetrahedron, vol. 52, No. 7, pp. 2435–2448, 1996.

(List continued on next page.)

Primary Examiner—Alan L. Rotman
Assistant Examiner—Taylor V Oh
(74) Attorney, Agent, or Firm—Bennett Jones LLP

(57) ABSTRACT

Non steroidal mimetics or analogues of brassinosteroids such as brassinolide include two bicyclic subunits each having a vicinal diol group and a polar unit and linked by a linking moiety such that the vicinal diol groups and polar unit are closely superimposable on corresponding functional groups in the brassinosteroid.

14 Claims, 9 Drawing Sheets

OTHER PUBLICATIONS

Yokota, et al., Molecular Structure and Biological Activity of Brassinolide and Related Brassinosteroid Article in CRC Press, Boca Raton, Florida, 1992, pp. 317–340.

Takatsuto, et al. "Structure Activity Relationship of Brassinosteroids" Article in Physochemistry, vol. 22, No. 11, pp. 2437–2441.

Thompson, et al. "Synthesis of Brassinosteroids and Relationshiop of Structure to Plant Growth–Promoting Effects" Article in Steroids, 1982, pp. 89–105.

Luo, et al. "Bioactivity of Brassinolide Methyl Ethers" Article Phytochemistry, vol. 49, No. 3, pp. 637–642, 1998.

Seto, et al. "2,3,5–Tri–epi–brassinolide: preparation and biological activity in rice lamina inclination test", Article in Phytochemistry, 1999, pp. 815–818.

Baron, et al. "Structure—Activity Studies of Brassinolide B–Ring Analogues", Article in Phytochemistry Vo. 49, No. 7, pp. 1849–1858.

Back, et al. "Synthesis and Biological Activity of 25–Methoxy–, 25–Fluoro–, and 25–Azabrassinolide and 25–Fluorocastasterone: Surprising Effects, etc", Article in J. Orig. Chem., 1999, pp. 5494–5498.

Back, et al. "Effect of Chain Length and Ring Size of Alkyl and Cycloackyl Side–Chain Substitutents etc.", Article in J. Orig. Chem, 2000, pp. 3047–3052.

Mori, et al. "Synthesis of 25–Methyldolichosterone, 25–Methyl–2,3–diepidolchosterone, 25–Methylcastasterone and 25–Methylbrassinolide" article in Liebigs Ann. Chem. pp. 815–818.

Brosa, et al. "Synthesis and Molecular Modeling: Related Approaches to Progress in Brassinosteroid Research" Article in Lipids, vol. 32, No. 12 (1997) pp. 1341–1347.

Stoldt, et al. "Side Chain Conformation of the Growth–Promoting Phytohormones Brassinolide and 24–Epibrassinolide" Article in Mag. Resonance in Chemistry, vol. 35, pp. 629–636.

Takeno, et al. "Brassinosteroid–Induced Bending of the Leaf Lamina of Dwarf Rice Seedlings: An Auxin–Mediated Phenomenon" article Plant & Cell Physiol. pp. 1275–1281.

Sung, et al. "Synthesis and bioactivity of 6a– and 6b–hydroxy analogues of castasterone" Article in Phytochemistry 55 (2000) pp. 121–126.

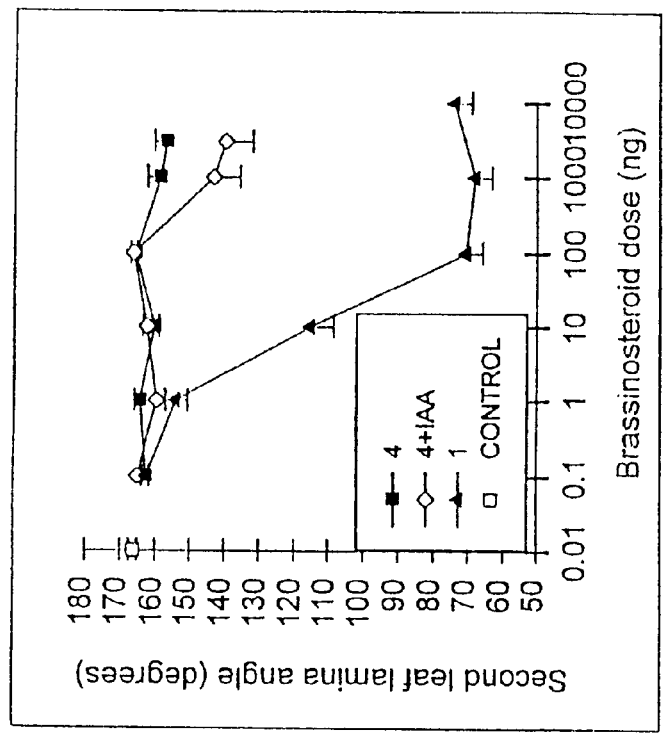
Figure 9. Bioassay of Mimetic 4
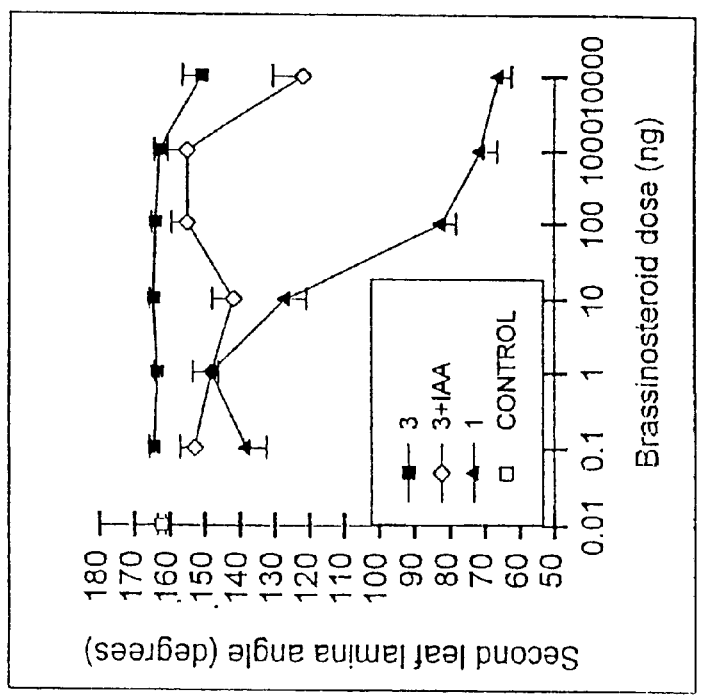
Figure 8. Bioassay of Mimetic 3

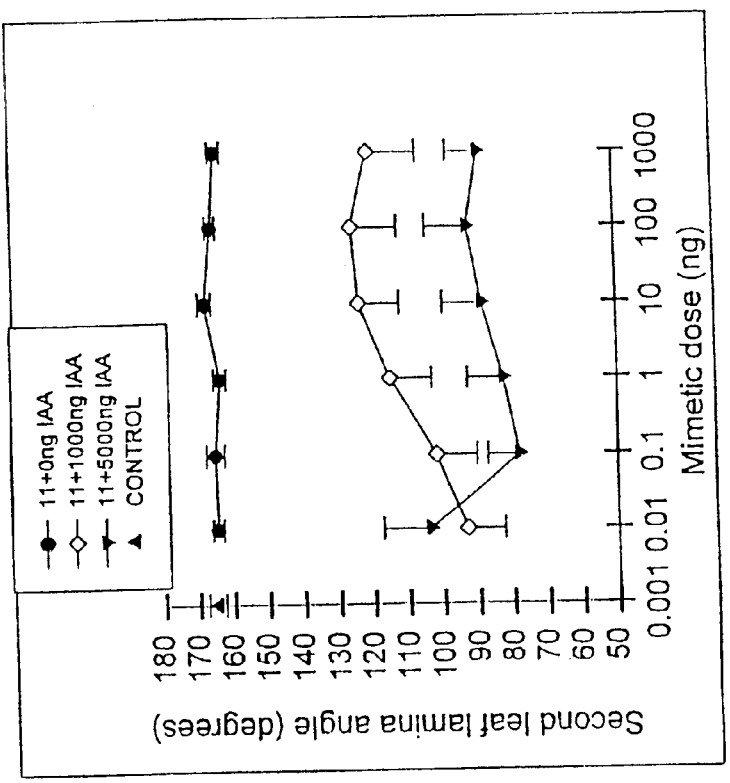
Figure 11. Bioassay of Mimetic 11
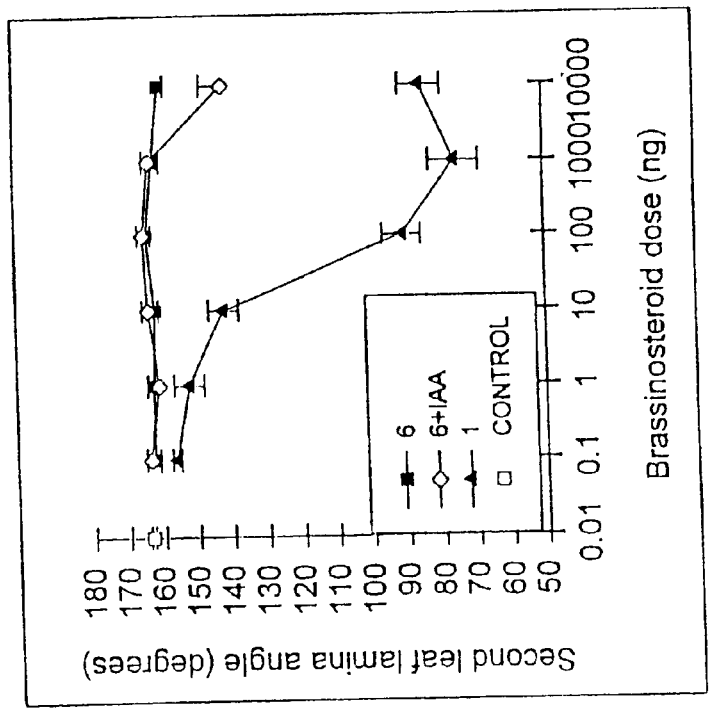
Figure 10. Bioassay of Mimetic 6

NON-STEROIDAL MIMETICS OF BRASSINOLIDE

This application claims the benefit of Provisional Application No. 60/251,039, filed Dec. 5, 2000.

FIELD OF THE INVENTION

The present invention relates to non-steroidal mimetics of brassinolide and methods of their synthesis and use.

BACKGROUND

Brassinolide (22R, 23R, 24S)-2α,3α,22,23-tetrahydroxy-24-methyl-B-homo-7-oxa-5α-cholestan-6-one, is a powerful plant growth-regulator.[1] It manifests biological activity when applied exogenously at doses as low as one ng per individual plant to species such as rice, beans and others. Although brassinolide and related brassinosteroids such as castasterone are widespread throughout the plant kingdom, natural sources of brassinosteroids are an impractical source of these compounds because of their very low concentrations (typically ppb to ppt). While several syntheses of brassinolide and its analogues have been reported[2], synthetic brassinosteroids are generally too expensive for most commercial applications. Despite the poor availability of brassinosteroids, a great deal of effort has been expended on investigations of their chemistry, biological properties, field applications, and molecular biology[3-5]. The discovery of alternative novel compounds capable of mimicking the biological activity of natural brassinosteroids would thus clearly be of considerable benefit if their synthesis were simpler and more cost-effective.

Numerous structure-activity studies of brassinosteroids have been reported[3-13]. In general, they reveal that the vicinal diol groups and the configurations of their stereocenters are of importance in maintaining high bioactivity. Certain methyl ether derivatives are also highly active[14]. The 5α-configuration is required for optimum activity[15], but the B-ring tolerates considerable variation, providing that the presence of a polar functional group, which does not have to be a lactone, is maintained[16]. Numerous side chain variations have also been shown to result in high bioactivity[17].

SUMMARY OF THE INVENTION

The present invention comprises nonsteroidal brassinolide mimetics, methods of synthesizing such mimetics and methods of their use. Molecular modeling was used to determine the minimum energy conformation of brassinolide, which served as a starting point for the rational design of these nonsteroidal analogues. Modeling was followed by synthesis, using the procedures described herein. Potential mimetics were then bioassayed to determine their biological activity relative to brassinolide.

In one aspect, the invention comprises a non-steroidal mimetic of a brassinosteroid having two vicinal pairs of hydroxyl groups and a B-ring polar group, said mimetic comprising:
(a) two bicyclic subunits, wherein each subunit comprises a vicinal diol group in which the hydroxyl groups of each vicinal pair are cis and in a gauche relationship;
(b) a polar group attached to one bicyclic unit, said polar group corresponding to the B-ring polar group of a brassinosteroid; and
(c) a linker which joins the two bicyclic subunits such that each vicinal pair of hydroxyl groups and the polar group is substantially superimposed on the vicinal pairs and the B-ring lactone moiety of brassinolide respectively.

In one embodiment, the mimetic is a compound having the formula having the formula:

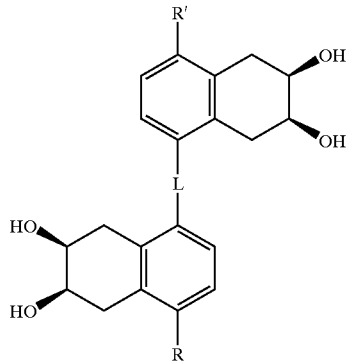

wherein L represents an acetylene linker or a trans-ethylene linker, R represents a polar functional group, and R' represents hydrogen or hydroxy. In another embodiment, the mimetic is a compound having the formula:

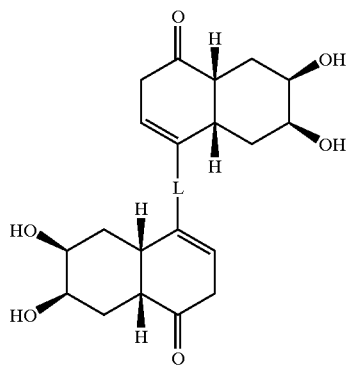

where L represents trans-ethylene.

The compounds of the present invention may also include those in which one or more of the hydroxyl groups are protected with removable protecting groups, such as hydrolyzable esters, ketals or acetals. As used herein, "protected hydroxyl" refers to a group which is readily converted to hydroxyl, for example, a hydrolyzable ester, a lower alkyl (i.e. $C_1$ to $C_6$), benzyl, trityl, allyl, or alkylsilyl ether, or an acetal (alkoxyalkyl ether). Since the hydroxyl groups of the subject compounds form cis-diols, cyclic acetals or ketals, e.g. acetonides, may also be used as protecting groups. Such protecting groups are widely used in organic synthesis and in preparation of prodrugs and are well known in the art. The protected hydroxyl form of the compound may itself have biological activity either per se or resulting from conversion or hydrolysis after application of the compound to the plant being treated.

In specific embodiments of the invention, the mimetics comprise four non-steroidal brassinolide analogue compounds, each with biological activity. These four compounds are:
(a) (±)-1,2-bis[4,6α,7α-trihydroxy-5,6,7,8-tetrahydronaphthyl]ethyne (mimetic 3) and its meso isomers;
(b) 1-[4,6α,7α-trihydroxy-5,6,7,8-tetrahydronaphthyl]-2-[6α',7α'-dihydroxy-5',6',7',8'-tetrahydronaphthyl]ethyne (mimetic 4) as two diastereomeric (±) pairs;

(c) (E)-(±)-1,2-bis[4,6α,7α-trihydroxy-5,6,7,8-tetrahydronaphthyl]ethene (mimetic 6) and its meso isomer; and (d) (E)-(±)-1,2-bis[trans-(4aα,8aβ-4-oxo-6α,7α-dihydroxy-4a,5,6,7,8,8a-hexahydro-(3H)-naphthyl]ethene (mimetic 11) and its meso isomer; or esters thereof.

In another aspect of the invention, there are provided methods for synthesizing non-steroidal mimetics of a brassinosteroid and methods and compositions for using such mimetics. In one aspect, the invention may comprise a method of promoting a desired tissue morphology and/or physiological state in a higher plant, wherein said desired tissue morphology or physiological state is selected from at least one of: shoot growth, grain, seed or fruit yield enhancement, root (radicle) growth retardation, improved fruit set and fruit quality or other desired tissue morphology or physiological state that is promoted by a brassinosteroid, said method comprising the step of applying an effective amount of a mimetic as claimed herein in a suitable delivery vehicle.

BRIEF DESCRIPTION OF THE FIGURES

FIG. 8: Bioactivity of mimetic 3 in the rice leaf lamina inclination assay.

FIG. 9: Bioactivity of mimetic 4 in the rice leaf lamina inclination assay.

FIG. 10: Bioactivity of mimetic 6 in the rice leaf lamina inclination assay.

FIG. 11. Bioactivity of mimetic 11 in the rice leaf lamina inclination assay.

DETAILED DESCRIPTION OF THE INVENTION

When describing the present invention, the following terms have the following meanings, unless indicated otherwise. All terms not defined herein have their common art recognized meanings.

The term "mimetic" refers to a brassinosteroid analogue which possesses statistically significant brassinosteroid activity when subjected to the rice leaf lamina inclination bioassay and applied in a dose of about 10,000 ng or less, with or without a dose of a plant growth regulator such as an auxin such as IAA. In this description, the term "mimetic" may also be used in reference to a compound which was considered a potential mimetic but did not display statistically significant bioactivity when tested.

The term "non-steroidal" refers to compounds lacking the 17-carbon fused tetracyclic structure characteristic of steroids.

1. Design and Molecular Modeling of Mimetics

Figure 1:
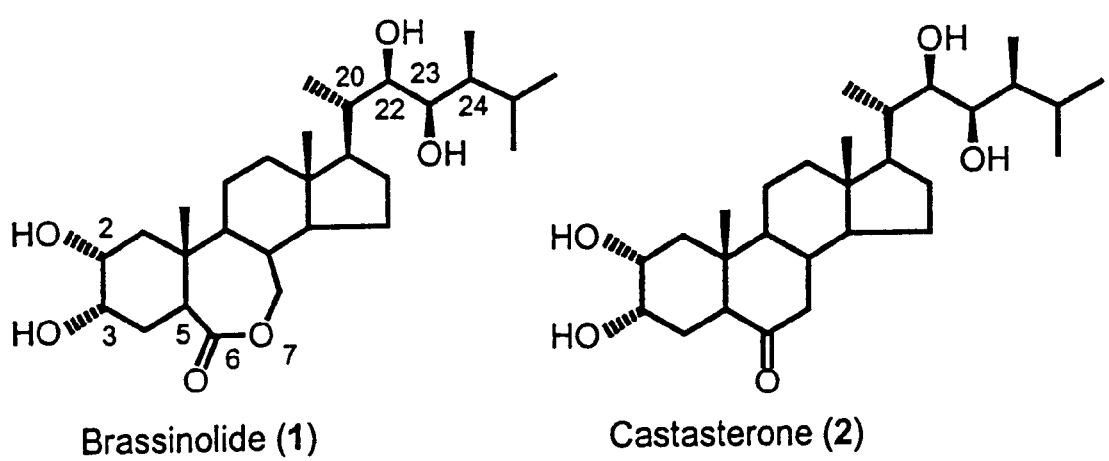
FIG. 1: (Prior Art) Structure of brassinolide (1) and castasterone (2)

The structures of brassinolide and castasterone are shown in FIG. 1. Applicants believed that two rigid subunits containing vicinal diol groups, joined by an appropriate linker, would permit close superimposition of individual key functional groups upon those of brassinolide. A gauche relationship between the hydroxyl groups of each vicinal pair and an additional hydroxyl or keto group in the B-ring to satisfy the requirement for a polar functionality were also deemed by Applicants to be necessary.

Figure 2:
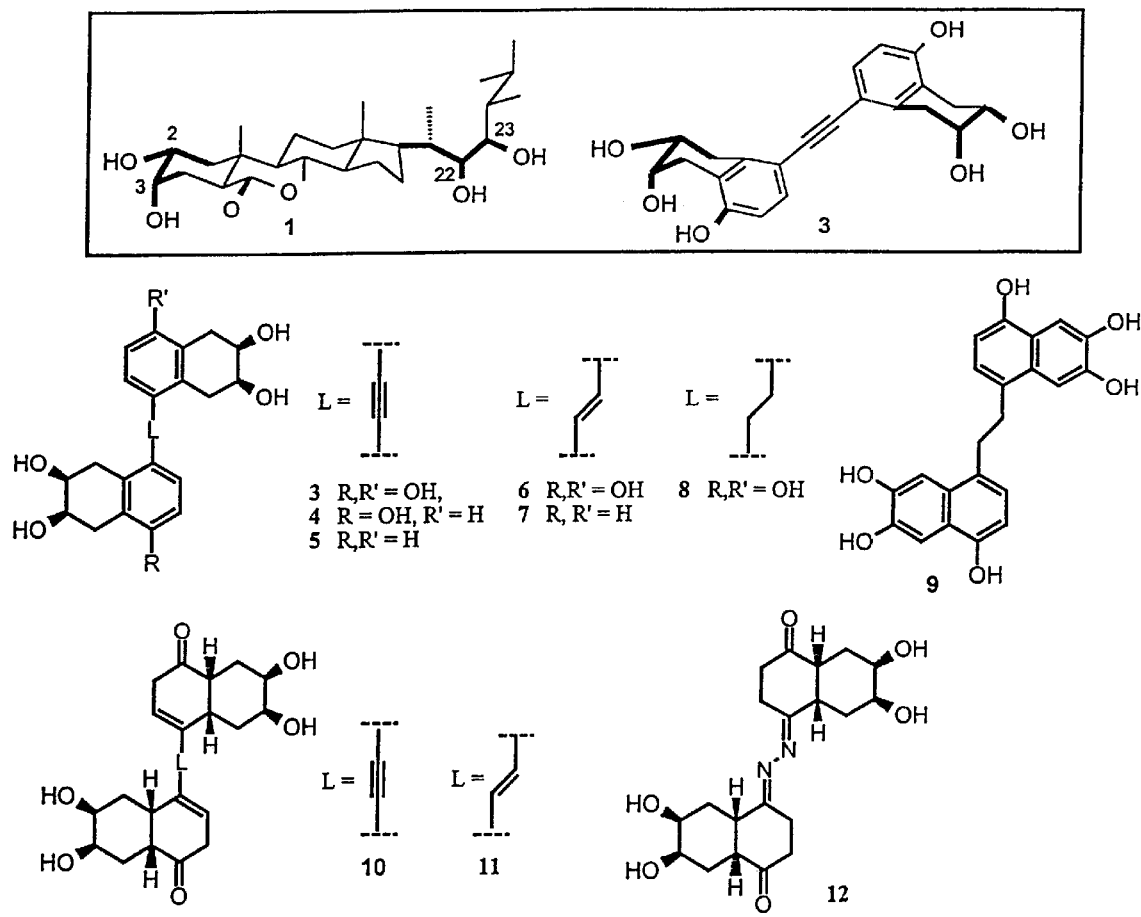
FIG. 2: Conformation of brassinolide and mimetic 3, and structures of mimetics 3 to 12.

A prototype brassinosteroid mimetic (3) is shown in FIG. 2, with key structural features highlighted. Compounds 4–12, also shown in FIG. 2, are other structures which are mimetics or included for purposes of comparison.

A series of bicyclic subunits containing the key diol groups, and generally an additional hydroxyl or keto group to mimic the polar B-ring functionality of natural brassinosteroids such as brassinolide or castasterone, were linked by means of acetylene, trans-alkene, —CH$_2$CH$_2$— and azine linkers (FIG. 2), affording structures that superimposed closely with brassinolide. For convenience, only the stereoisomers that most closely resemble brassinolide are shown in the Figures and only these were the subjects of molecular modeling studies.

The relative spatial orientation of the alcohol moieties of brassinolide is illustrated in FIG. 2. The conformation was determined by an initial MM2 minimization, followed by a Monte Carlo search using MacroModel® to locate the global minimum energy conformation, and finally by ab initio refinement with Spartan® (STO 3G basis set)[18]. The minimum energy conformation of brassinolide was then used as a starting point for the rational design of the various nonsteroidal analogues. The modeling (vide infra) of some of the mimetic structures showed remarkable overlap of the key hydroxyl groups with the vicinal diol functionalities of brassinolide. The inclusion of phenolic hydroxyl groups in the subunits of mimetics 3, 4, 6, 8 and 9 (FIG. 1), instead of ketone or lactone carbonyl groups as found in castasterone and brassinolide, respectively, was validated by the observation that reduction of the 6-keto group of castasterone afforded a pair of C-6 alcohol epimers that were both significantly bioactive[19]. Mimetics 5 and 7, where both subunits lack polar functions at this position, and mimetic 9, where the hydroxyl groups of the diol units are coplanar instead of gauche, were included for comparison.

Molecular modeling of representative structures 3, 6, 10, 11 and 12 as well as of brassinolide (1), is summarized in Table 1.

TABLE 1

| | Interatomic distances (Angstrom units) | | | | | |
|---|---|---|---|---|---|---|
| | Compound | | | | | |
| Atoms | 1 | 3 | 6 | 10 | 11 | 12 |
| O2–O3 | 2.81 | 2.82 | 2.83 | 2.66 | 2.74 | 2.78 |
| O22–O23 | 2.67 | 2.84 | 2.83 | 2.77 | 2.78 | 2.75 |
| O2–O22 | 11.36 | 9.92 | 10.87 | 9.29 | 10.98 | 11.18 |
| O2–O23 | 13.77 | 11.90 | 12.56 | 11.46 | 12.62 | 12.17 |
| O3–O22 | 10.94 | 10.38 | 10.96 | 9.90 | 11.11 | 11.41 |
| O3–O23 | 13.49 | 12.61 | 13.12 | 12.25 | 13.20 | 12.58 |

With the exception of mimetic 12, the global minimum energy conformations of the mimetics were determined by MM2 minimization, followed by Monte Carlo searches using MacroModel®. These structures were then imported into Spartan® and subjected to further semi-empirical AM1 geometry optimization and calculation of their heats of formation. For mimetic 12, the minimum energy conformation was determined directly with Spartan®. To obtain optimum superimposition of the hydroxyl groups of the acetylene-linked mimetics 3 and 10 with the hydroxyl groups of brassinolide, it was necessary to constrain key dihedral angles to match those in brassinolide. Geometry optimization and energy minimization of the constrained structures with Spartan® (semi-empirical, AM1) indicated that their energies were 6.5 and 0.6 kJ/mole, respectively, higher than those of their respective global energy minima. The constrained conformations are therefore readily accessible at room temperature through normal conformational interchange. Interatomic distances between the oxygen atoms of the vicinal diol moieties of brassinolide and the mimetics are presented in Table 1 and provide a measure of how well the mimetics resemble brassinolide.

Table 1 reveals that the largest structural discrepancies were noted for the interatomic distances between hydroxyl groups on separate subunits joined by acetylenic linkers. Thus, in mimetics 3 and 10, the interatomic distances O2-O22, O2-O23, O3-O22 and O3-O23 (the numbering system of brassinolide is used for all of the compounds for convenience) were all shorter than those in brassinolide, in some cases by more than 2 Å (i.e. O2-O22 and O3-O22 in mimetic 10). On the other hand, mimetics 6, 11 and 12, where trans-alkene or azine linkers connect the subunits, showed much better correspondence with brassinolide, with the largest differences reduced to 1.21 Å, 1.15 Å and 1.60 Å for O2-O23 between mimetics 6, 11 and 12 respectively, and brassinolide. The O-C-C-O dihedral angles of both diol moieties in all of the modeled compounds were in close accord with those of brassinolide, showing slightly compressed gauche conformations. Thus, all of the mimetics (3–12) have relatively low energy conformations that superimpose reasonably well with brassinolide, with mimetics 6, 11 and 12 providing the best fit of hydroxyl functions. It is important to note that the calculated conformations of brassinolide, as well as those of the mimetics, may be substantially different in the aqueous environment of biological systems where hydrogen-bonding with water may significantly affect their structures. Notwithstanding this limitation, molecular modeling provides a convenient means by which potential mimetics can be evaluated and refined.

2. Synthesis of Mimetics

For greater ease of synthesis, the mimetics are designed to generally be assembled from two identical subunits, thereby including a redundant hydroxyl or carbonyl group in the upper subunit of the coupled product. Mimetic 4 is constructed from two different subunits, thereby eliminating the redundant hydroxyl group. All of the mimetics in FIG. 2, except 9, exist as mixtures of stereoisomers because the chiral subunits were racemic and the coupled products (except 9) are formed as mixtures of diastereomers arising from pairs of matched and mismatched subunits. However, vicinal diol groups are introduced stereoselectively cis, and the decalin units in mimetics 10–12 are trans-fused. Since the stereoisomers are exceedingly difficult to separate, even by HPLC, bioassays (below) are performed on unseparated mixtures. Specific compounds may be referred to herein by name, by name and compound number or by compound number alone.

a) Mimetics 3, 4 and 5

Figure 3:
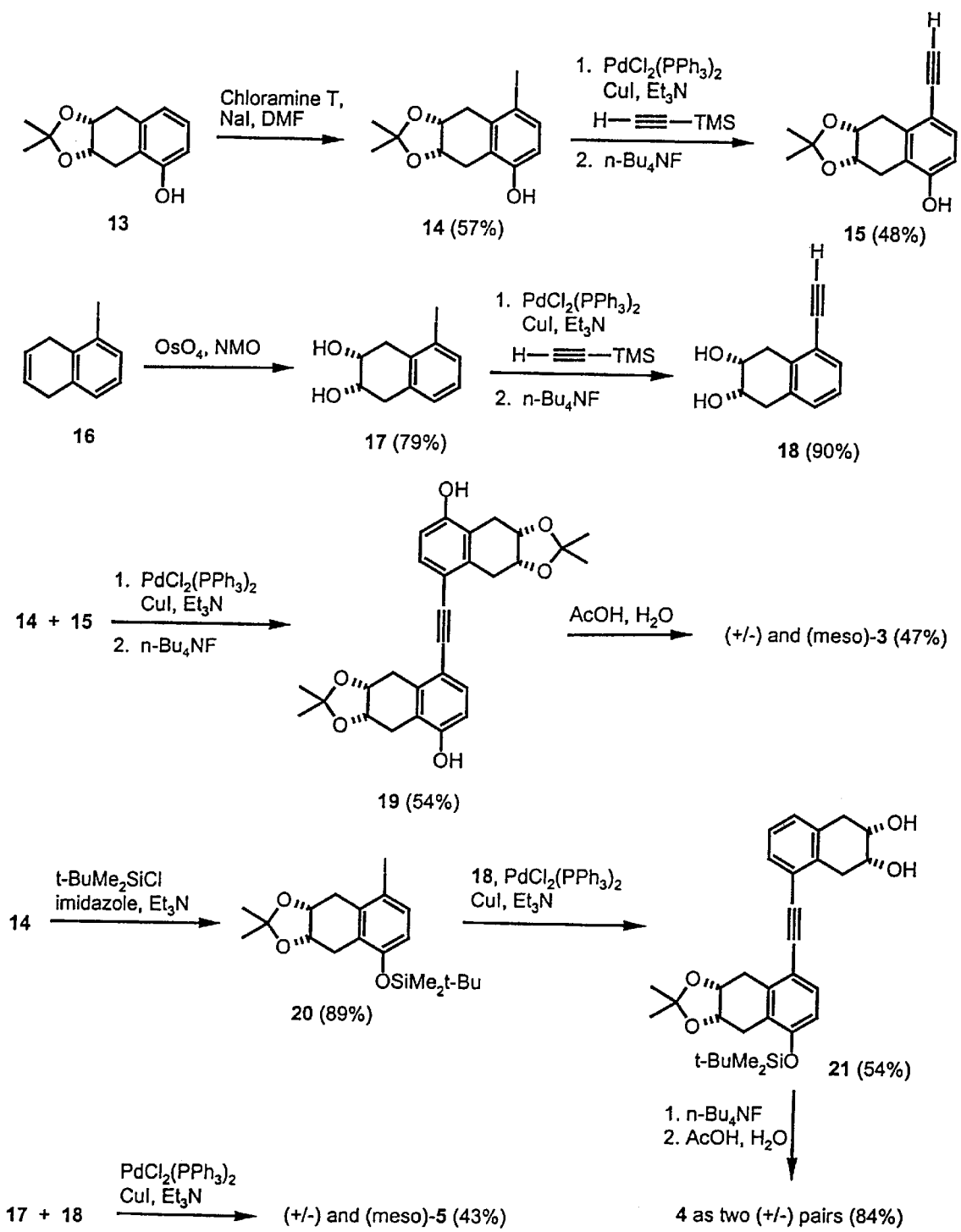
FIG. 3: Synthesis of mimetics 3, 4 and 5.

The synthesis of mimetics 3, 4 and 5 is shown in FIG. 3. Tetrahydronaphthalene (13) is obtained from α-naphthol using published procedures[20a,b]. Iodination in the para position is effected with chloramine T and sodium iodide, as published[20c] to afford product (14). Sonogashira coupling[21] of (14) with trimethylsilylacetylene produces (15). The iodide (16) is 6 prepared from α-naphthylamine as reported previously[22]. Dihydroxylation and Sonogashira coupling then provides acetylene (18). Similar coupling of iodide (14) with acetylene (15), followed by deprotection of (19), affords the bis-phenol (3) as a mixture of the corresponding meso and (+/−) isomers, while the coupling of the silyl ether (20) with (18), followed by removal of protecting groups, produces the monophenol (4) as two diastereomeric (+/−) pairs. Finally, the coupling of (17) and (18) affords the mimetic (5), lacking phenolic hydroxyl groups, as a mixture of a meso compound and a (+/−) pair.

b) Mimetics 6, 7 and 8

Figure 4:
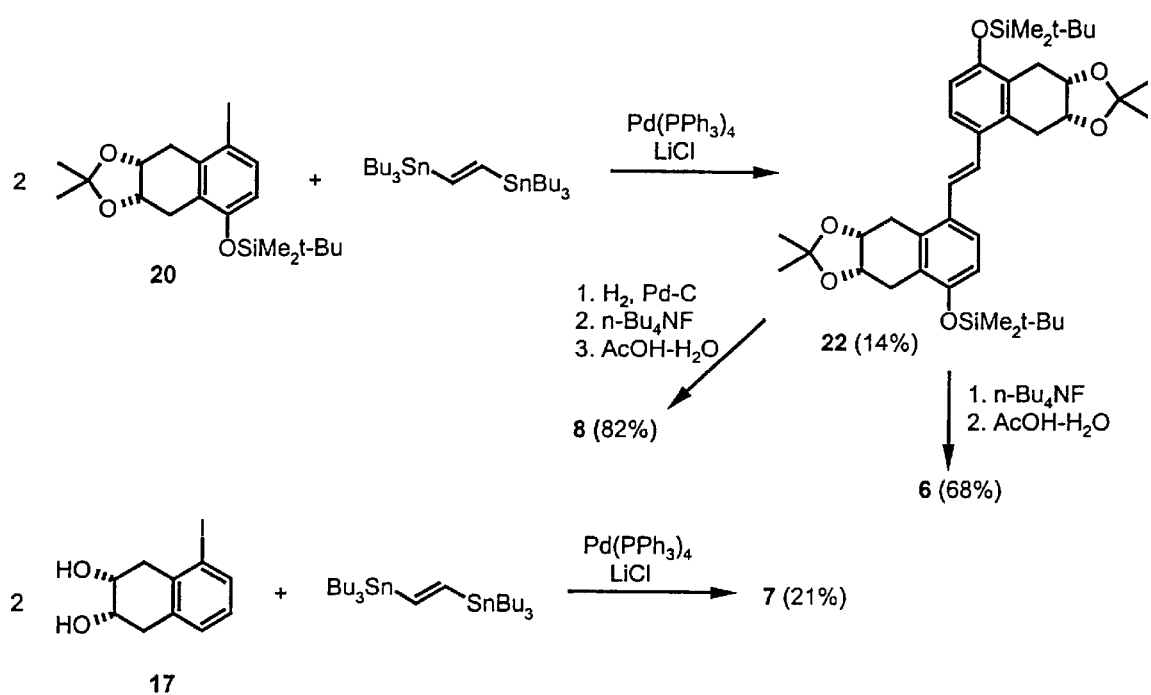
FIG. 4: Synthesis of mimetics 6, 7 and 8

Mimetics 6, 7 and 8 are prepared as shown in FIG. 4. Iodide (20) is subjected to Stille coupling[23] with trans-bis (tri-n-butylstannyl)ethylene[24], to afford (22) in one step, but in low yield. Deprotection provides mimetic 6 as a mixture of a meso compound and a (+/−) pair. Hydrogenation and deprotection of (22) produces mimetic 8 in the form of a similar mixture of stereoisomers. Mimetic 7, which is devoid of phenolic hydroxyl groups, is similarly prepared from (17) and trans-bis(tri-n-butylstannyl)ethylene.

c) Mimetic 9

Figure 5:
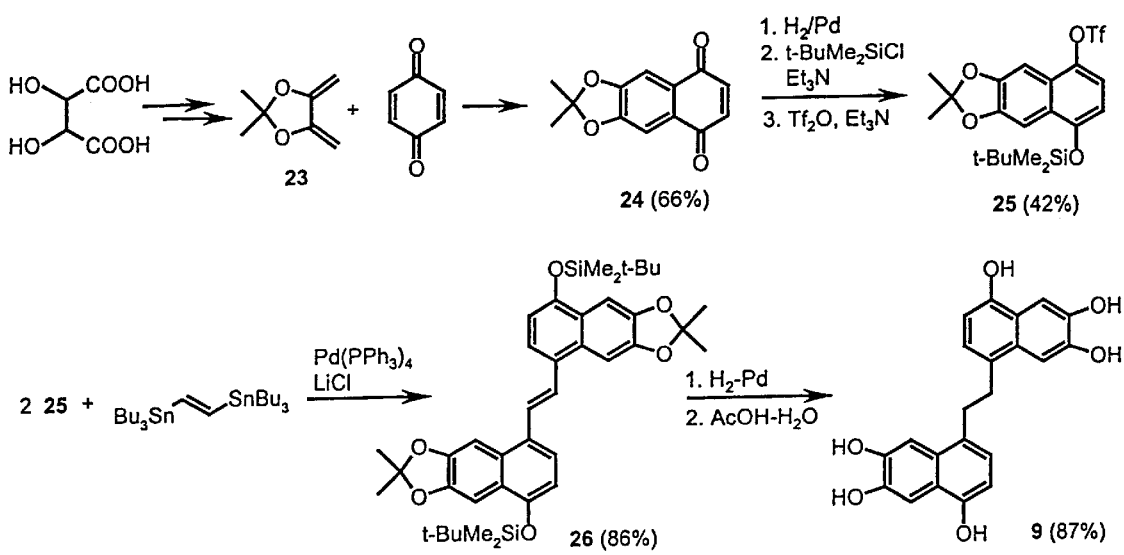
FIG. 5: Synthesis of mimetic 9

The naphthalene-based mimetic 9 is obtained as outlined in FIG. 5. The diene (23) is obtained from tartaric acid by published procedures[25]. Its Diels-Alder cycloaddition with benzoquinone provides (24), which is hydrogenated to the corresponding 1,4-dihydroxynaphthalene, followed by silylation of one phenolic hydroxyl group and conversion of the other to its triflate. Stille coupling of the resulting triflate (25) with trans-bis(tri-n-butylstannyl)ethylene affords (26). Direct deprotection of the six phenolic groups of the latter results in a product that is easily oxidized by air, thereby obviating its potential utility as a brassinosteroid mimetic. However, hydrogenation of the trans-ethylene linker prior to deprotection affords the more stable product (9).

d) Mimetics 10, 11 and 12

Figure 6:
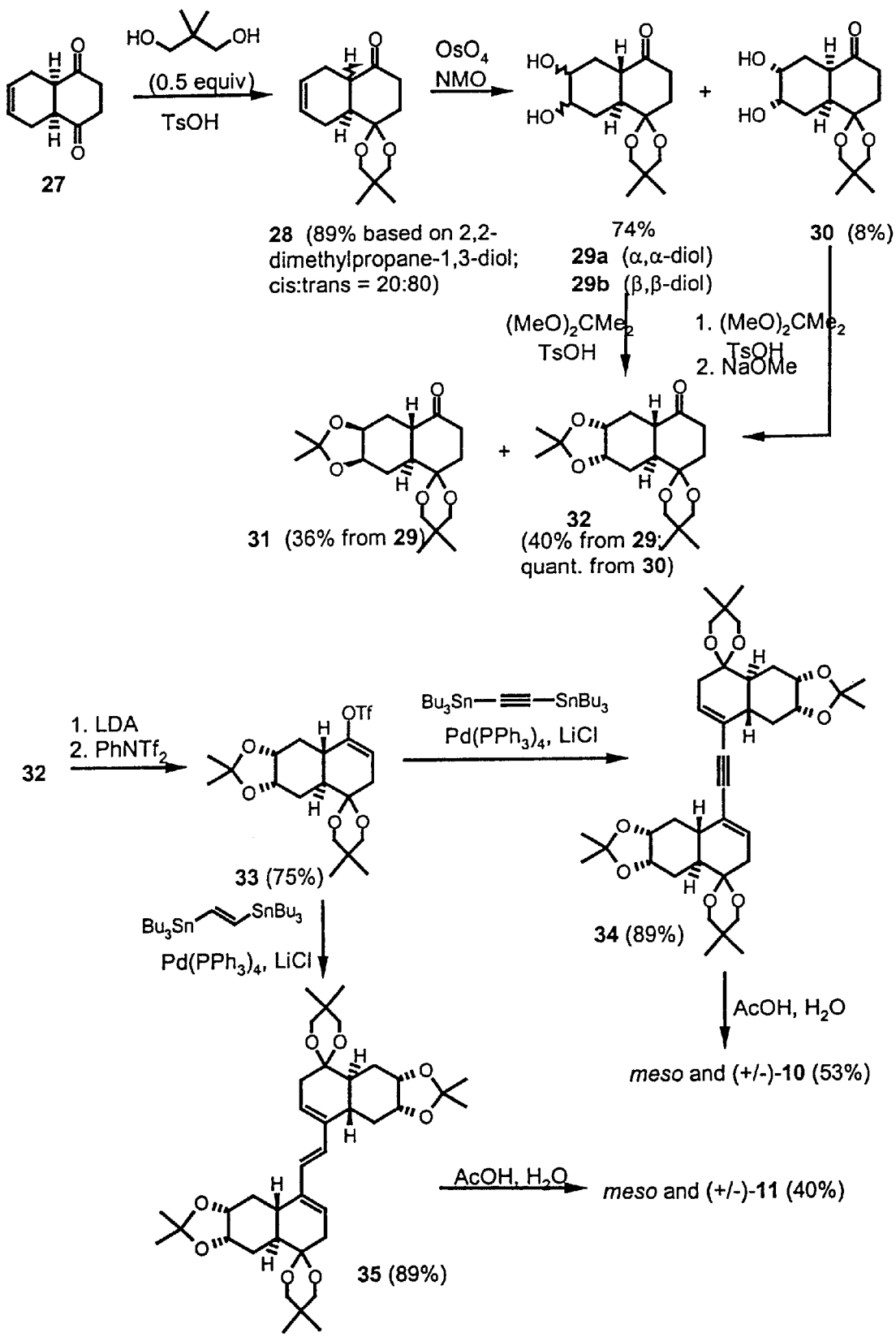
FIG. 6: Synthesis of mimetics 10 and 11
Figure 7:
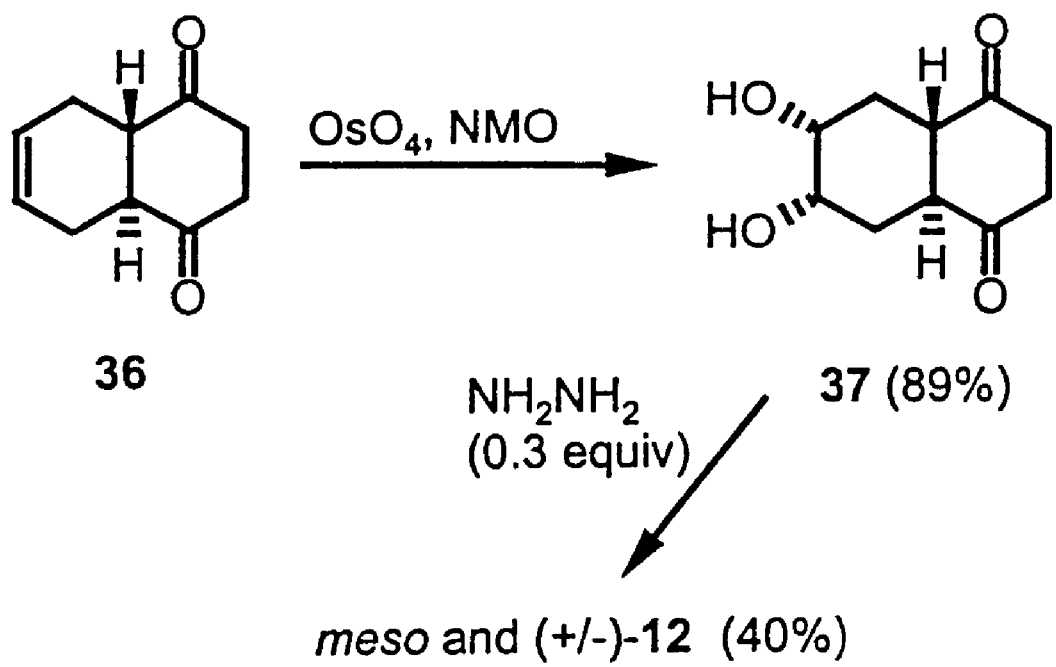
FIG. 7: Synthesis of mimetic 12

Mimetics 10, 11 and 12, are prepared as shown in FIGS. 6 and 7. These mimetics are based on the trans-decalone subunit, prepared from (27), which is in turn derived from the Diels-Alder cycloaddition of benzoquinone and 1,3-butadiene, using published procedures[26]. Monoprotection of (27) to (28) is accompanied by extensive epimerization to the more stable trans-decalone isomer. The mixture is subjected to cis-dihydroxylation to afford (29) as an unseparable mixture of trans-fused α,α- and β,β-diol isomers, along with the α,α-diol (30), obtained as the sole product from the cis-fused system, and easily separable from (29). Further ketalization of the diol moiety of (29) produces separable acetonide epimers (31) and (32). Moreover, similar ketalization of (30), followed by quantitative base-catalyzed epimerization via the corresponding enolate, provides additional (32). The assignment of the 6α,7α configuration to (30) is made on the basis of previous reports that dihydroxylation of similar unsaturated cis-fused decalins proceeds stereoselectively from the less hindered exo face[27]. Furthermore, since (30) is epimerized exclusively to (32) and not to (31), this also confirms the assignment of (32) as the 6α,7α-isomer.

Stereoisomer (32) is then converted into the corresponding enol triflate (33), followed by Stille coupling with either bis(tri-n-butylstannyl)acetylene[28] or trans-bis(tri-n-butylstannyl)ethylene[24] and deprotection, to afford the desired products, mimetics 10 and 11, respectively, each obtained as a mixture of meso- and (+/−)-stereoisomers. Finally, cis-dihydroxylation of the trans-fused decalone (36)[29] provides diol (37). The latter is treated with only 0.25 equivalents of hydrazine to minimize polymerization and affords the corresponding azine (12) as a mixture of stereoisomers. The preparation of azine (12) from the monoketone (32) and hydrazine failed because of decomposition during attempts to remove the ketal protecting groups (FIG. 6).

3. Bioactivity

Mimetics 3–12, along with brassinolide for comparison, were subjected to the rice leaf lamina inclination bioassay[30]. This technique is a rapid, highly sensitive and convenient means for detecting and measuring brassinosteroid bioactivity. Strongly active brassinosteroids such as brassinolide can be readily detected at doses as low as 1 ng/plant. The assay is based on the downward movement response of the second leaf lamina angle of rice seedlings to the application of active brassinosteroids. Thus, a decrease in the leaf angle occurs from about 160 degrees (i.e. nearly upright) in control plants to angles of less than 90 degrees when a strong response is measured. A plot of leaf lamina angle vs. the logarithm of the dose in ng provides a convenient indication of bioactivity.

Brassinosteroids show synergy with auxins such as indole-3-acetic acid (IAA) in this bioassay[7,30,31]. Thus, co-application of a given dose of the brassinosteroid with IAA generally elicits a similar decrease in the leaf lamina angle as would be observed with a dose one or two orders of magnitude higher of the brassinosteroid alone. IAA is without significant effect in this bioassay when applied on its own. The bioassays of mimetics 3–12 were therefore run both in the presence and absence of 1000 ng of added IAA and mimetic 11 was also bioassayed in the presence of 5000 ng of IAA.

Mimetics 5 and 7, which lack a polar functional group corresponding to the B-ring lactone moiety of brassinolide, are completely inactive at all dosage levels, with or without IAA application. Similarly, mimetics 8 and 9, containing a saturated linker, display no bioactivity (data not shown for mimetics 5, 7, 8 and 9). However, mimetics 3 and 4, where an acetylenic linker joins subunits containing at least one phenolic group to satisfy the need for a polar B-ring function, show modest, but statistically significant activity when applied together with IAA in 95% ethanol. The results are shown in FIGS. 8 and 9, which indicate that the highest dose of 10,000 ng of mimetic 3, and the two highest doses of mimetic 4 (1000 and 10,000 ng) produced a significant bioassay response. Mimetic 6 contains identical subunits to 3, but employs a trans-ethylene linker. It too shows significant bioactivity, but only at a dose of 10000 ng when applied together with IAA in 95% ethanol (FIG. 10). Error bars in FIGS. 8–10 indicate standard error. Finally, the trans-decalone-based mimetics 10 and 12, possessing acetylenic and azine linkers, respectively, are devoid of activity at all doses even with the coapplication of IAA (data not shown). In contrast to the inactive or weakly active mimetics 3–10, and 12, mimetic 11, the structure of which is very closely superimposable upon brassinolide, is active across a wide range of doses when applied together with 1000 ng of IAA (FIG. 11). For mimetic 11 a small amount of DMSO is used as an initial solvent (because of poor solubility in ethanol), and then the DMSO solution is diluted with a 2.5% aqueous solution of the ICI formulating agent, Atlas®. The activity of mimetic 11 under these circumstances is even further enhanced when the amount of IAA is increased to 5000 ng (FIG. 11). Under these optimum conditions, mimetic 11 displays significant activity even at the very low dose of 0.01 ng. It is worth noting that in FIG. 11 error bars represent confidence limits of 95%, (P=0.05). Control experiments with IAA, DMSO and Atlas®, but without the mimetic, showed no significant activity.

4. Examples

The following examples are intended to illustrate but not limit the invention. If an abbreviation is not defined, it has its generally accepted meaning.

A. General Methods

NMR spectra were recorded on a Bruker ACE 200 or AM 400 spectrometer. NMR signals from diastereomeric products generally coincided and could not be resolved, except where otherwise noted. $^1$H NMR integrations are based on one subunit for symmetrical products. Where $^{13}$C NMR signals are listed as C, CH, $CH_2$ or $CH_3$, the assignments were made on the basis of DEPT experiments. Chromatography was performed on flash grade silica-gel unless indicated otherwise.

B. Synthesis of Precursor Molecules used to Synthesize Mimetics 3–12 a) Compound 14: (±)-4-Iodo-6α,7α-(isopropylidenedioxy)-5,6,7,8-tetrahydro-1-naphthol Compound (13)[20] (0.99 g, 4.50 mmol) was dissolved in 10 mL of DMF. Subsequent addition of sodium iodide (808 mg, 5.40 mmol) and chloroamine-T trihydrate (1.52 g, 5.40 mmol) resulted in a murky, yellowish-green solution, which was stirred for 2.75 h at room temperature. The mixture was diluted with water, acidified with 10% HCl solution, and extracted several times with ether. The combined ether layers were washed with 5% $NaHSO_3$ and NaCl solutions, dried ($MgSO_4$), evaporated in vacuo, and purified by chromatography (elution with 5% ethyl acetate-hexanes) to afford 892 mg (57%) of compound (14): mp 172–175° C. (from methylene chloride-hexanes); IR (KBr) 3249, 1591, 1188, 1040 $cm^{-1}$; $^1$H NMR (400 MHz, $CDCl_3$—$CD_3OD$) δ 7.54 (d, J=8.5 Hz, 1H), 6.48 (d, J=8.5 Hz, 1H), 5.32 (s, 1H, OH), 4.63–4.61 (m, 2H), 3.18 (m, 2H), 2.74 (m, 1H), 2.56 (m, 1H), 1.33 (s, 3H), 1.14 (s, 3H); $^{13}$C NMR (100 MHz, $CDCl_3$—$CD_3OD$) δ 154.4 (C), 139.2 (C), 136.5 (CH), 123.7 (C), 115.6 (CH), 108.1 (C), 87.8 (C), 74.2 (CH), 73.9 (CH), 38.7 ($CH_2$), 26.7 ($CH_2$), 26.0 ($CH_3$), 24.2 ($CH_3$); mass spectrum, m/z (relative intensity, %) 346 ($M^+$, 25), 331 (34), 288 (37), 144 (67), 43 (100). Analysis calculated for $C_{13}H_{15}IO_3$: C, 45.11; H, 4.37; found: C, 45.18; H, 4.46.

b) Compound 15: (±)-4-Ethynyl-6α,7α-(isopropylidenedioxy)-5,6,7,8-tetrahydro-1-naphthol Compound (14) (500 mg, 1.44 mmol) was dissolved in 7 mL of dry 1,4-dioxane and 7 mL of dry triethylamine. Dichlorobis(triphenylphosphine)palladium(II) (10 mg, 1 mol %), copper(I) iodide (5.5 mg, 2 mol %), and (trimethylsilyl)acetylene (407 μL, 2.88 mmol) were added and the mixture was stirred at 70° C. for 24 h. The mixture was diluted with ethyl acetate and the aqueous layer was acidified with 10% HCl solution and extracted with ethyl acetate. The combined organic layers were washed with $NaHCO_3$ and NaCl solutions, dried ($Na_2SO_4$), and evaporated. The crude coupled material was dissolved in 20 mL of THF and tetra-n-butylammonium fluoride (2.0 mL of a 1.0 M solution in THF, 2.0 mmol) was added and the mixture was stirred at room temperature for 3 h. The reaction was concentrated in vacuo and diluted with ethyl acetate, washed with NaCl solution, dried ($Na_2SO_4$), concentrated in vacuo, and the residue was purified by chromatography (elution with 30% ethyl acetate-hexanes) to furnish 168 mg (48%) of compound (15): mp 152–156° C. (from acetonitrile); IR (KBr) 3260, 2437, 1590, 1160, 696; $^1$H NMR (400 MHz, $CDCl_3$) δ 7.28 (d, J=8.6 Hz, 1H), 6.63 (d, J=8.3 Hz, 1H), 5.18 (s, 1H, OH), 4.65–4.63 (m, 2H), 3.32 (dd, J=15.3, 3.6 Hz, 1H), 3.17 (s, 1H), 3.11 (dd, J=16.6, 3.4 Hz, 1H), 2.77 (dd, J=15.1, 3.4 Hz, 1H), 2.57 (dd, J=15.2, 3.4 Hz, 1H), 1.33 (s, 3H), 1.15 (s,3H); $^{13}$C NMR (100 MHz, $CDCl_3$—$CD_3OD$) δ 154.4 (C), 140.0 (C), 131.3 (CH), 121.8 (C), 113.3 (CH), 112.9 (C), 108.0 (C), 82.4 (C), 78.7 (CH), 76.7 (CH), 73.9 (CH), 31.7 ($CH_2$), 26.2 ($CH_3$),4% 26.0 ($CH_2$), 24.3 ($CH_3$); mass spectrum, m/z (relative intensity, %) 244

($M^+$, 52), 229 (58), 186 (90), 169 (80), 43 (100). Exact mass calculated for $C_{15}H_{16}O_3$: 244.1099; found: 244.1094.

c) Compound 17: (±)-5-Iodo-1,2,3,4-tetrahydro-2α,3α-naphthalenediol

Osmium tetroxide (1.7 mL of a 0.39 M solution in t-butanol, 0.66 mmol) and 4-methylmorpholine N-oxide (1.61 g, 13.8 mmol) were added to a solution of 5-iodo-1,4-dihydronaphthalene[22] [compound (16)] (3.35 g, 13.1 mmol). The mixture was stirred for 2.5 h at room temperature, Florisil (1 g) and solid sodium thiosulfate (714 mg) were added, and the stirring was continued for 2 h before the solid was removed by filtration. The filtrate was evaporated in vacuo and the residue was chromatographed (elution with 40% ethyl acetate-hexanes) to afford 3.00 g (79%) of compound (17): mp 139–141° C. (from chloroform); IR (KBr) 3333, 1555, 1175, 1068, 1051, 773 $cm^{-1}$; $^1H$ NMR(200 MHz, $CDCl_3$) δ 7.71 (d, J=7.7 Hz, 1H), 7.10 (d, J=7.5 Hz, 1H), 6.84 (t, J=7.7 Hz, 1H), 4.10 (m, 2H), 3.01 (m, 4H), 2.08 (br s, 2H, 2 OH); $^{13}C$ NMR (50 MHz, $CDCl_3$—$CD_3OD$) δ 136.9 (CH), 136.0 (C), 135.2 (C), 129.2 (CH), 127.6 (CH), 102.2 (C), 69.4 (CH), 68.7 (CH), 40.7 ($CH_2$), 34.5 ($CH_2$); mass spectrum, m/z (relative intensity, %) 290 ($M^+$, 45), 272 (60), 232 (50), 145 (100), 115 (96), 91 (31), 77 (64). Analysis calculated for $C_{10}H_{11}IO_2$: C, 41.40; H, 3.82; found: C, 41.43; H, 3.81.

d) Compound 18: (±)-1-Ethynyl-5,6,7,8-tetrahydro-6α,7α-naphthalenediol

Dichlorobis(triphenylphosphine)palladium(II) (242 mg, 5 mol %) and copper(I) iodide (33 mg, 2.5 mol %) were added to a solution of compound (17) (2.00 g, 6.89 mmol) in 65 mL of dry 1,4-dioxane and 65 mL of dry triethylamine. Subsequently, (trimethylsilyl)acetylene (1.46 mL, 10.3 mmol) was added and the mixture was refluxed for 8 h, at which time a further 1.5 equivalents of (trimethylsilyl)acetylene (1.46 mL, 10.3 mmol), 2.5 mol % of dichlorobis-(triphenylphosphine)palladium(II) (121 mg), and 2.5 mol % of copper(I) iodide (33 mg) were added. The mixture was refluxed for 16 h before water was added. The mixture was acidified with 10% HCl solution and extracted with ethyl acetate. The combined organic layers were washed with NaCl solution, dried ($Na_2SO_4$), and evaporated in vacuo. The residue was dissolved in 100 mL of THF and was cooled to 0° C., followed by the addition of tetra-n-butylammonium fluoride (7.6 mL of a 1.0 M solution in THF, 7.6 mmol). The reaction was stirred for 5 h at room temperature, $NH_4Cl$ solution was added, and the mixture was extracted several times with ethyl acetate. The combined organic layers were washed with NaCl solution, dried ($Na_2SO_4$), concentrated under vacuum, and chromatographed (elution with 50% ethyl acetate-hexanes) to give 1.17 g (90%) of compound (18): mp 133–136° C. (from methanol-water); IR (KBr) 3360, 1579, 1054, 1007, 976 $cm^{-1}$; $^1H$ NMR (400 MHz, $CDCl_3$) δ 7.36 (m, 1H), 7.12 (m, 2H), 4.74 (br s, 2H, OH), 4.18 (m, 2H), 3.32 (s, 1H), 3.22 (dd, J=17.7, 5.3 Hz, 1H), 3.12 (dd, J=17.7, 6.5 Hz, 1H), 3.03 (m, 2H); $^{13}C$ NMR (100 MHz, $CDCl_3$) δ 135.8 (C), 133.6 (C), 130.3 (CH), 129.5 (CH), 125.6 (CH), 121.7 (C), 81.8 (C), 81.7 (CH), 68.7 (CH), 68.6 (CH), 48.8 ($CH_2$), 34.0 ($CH_2$); mass spectrum, m/z (relative intensity, %) 188 ($M^+$, 11), 170 ($M^+$–$H_2O$, 100), 128 (88), 115 (43). Analysis calculated for $C_{12}H_{12}O_2$: C, 76.57; H, 6.43; found: C, 76.47; H, 6.58.

e) Compound 19: (±)-1,2-Bis[4-hydroxy-6α,7α-(isopropylidenedioxy)-5,6,7,8-tetrahydronaphthyl]ethyne and its Meso Isomer Compound (14) (235 mg, 0.680 mmol) and compound (15) (166 mg, 0.680 mmol) were dissolved in 5 mL of dry 1,4-dioxane and 5 mL of dry triethylamine. To this mixture, dichlorobis(triphenylphosphine)palladium(II) (4.7 mg, 1 mol %) and copper(I) iodide (2.5 mg, 2 mol %) were added. The reaction mixture was refluxed for 18 h, acidified with 10% HCl solution, and extracted several times with ethyl acetate. The combined extracts were washed with $NaHCO_3$ and NaCl solutions, dried ($Na_2SO_4$), evaporated in vacuo, and chromatographed (elution with 5–20% ethyl acetate-hexanes) to afford 168 mg (54%) of the coupled product (19), which consisted of (±)- and meso-diastereomers that could not be separated. Compound (19) was recrystallized from ethyl acetate-hexanes: mp 268–272° C.; IR (KBr) 3340, 1589, 1159, 1047, 817 $cm^{-1}$; $^1H$ NMR (400 MHz, acetone-$d_6$) δ 7.24 (d, J=8.3 Hz, 1H), 6.77 (d, J=8.4 Hz, 1H,), 4.62 (m, 2H), 3.33 (ddd, J=15.2, 9.2, 3.7 Hz, 1H), 3.13 (ddd, J=15.2, 7.3, 3.7 Hz, 1H), 2.84 (dt, J=15.1, 4.7, Hz, 1H), 2.59 (ddd, J=15.3, 8.6, 4.2 Hz, 1H); the following signals are from resolved acetonide methyl groups of the two diastereomers: 1.26 (s, 1.5H), 1.25 (s, 1.5H), 1.06 (s, 1.5H), 1.04 (s, 1.5H); $^{13}C$ NMR (100 MHz, acetone-$d_6$) δ 155.4 (C), 139.9 (C), 139.8 (C), 131.1 (CH), 123.2 (C), 115.5 (C), 115.4 (C), 114.0 (CH), 108.3 (C), 108.2 (C), 90.9 (C), 74.8 (CH), 74.6 (CH), 32.8 ($CH_2$), 32.7 ($CH_2$), 27.0 ($CH_2$), 26.9 ($CH_2$), 26.6 ($CH_3$), 24.7 ($CH_3$); mass spectrum, m/z (relative intensity, %) 462 ($M^+$, 1), 185 (7), 142 (100), 100 (44). Exact mass calculated for $C_{28}H_{30}O_6$: 462.2042; found: 462.2050.

f) Compound 20: (±)-1-t-Butyldimethylsilyloxy-4-iodo-6α,7α-(isopropylidenedioxy)-5,6,7,8-tetrahydronaphthalene Compound (14) (667 mg, 1.92 mmol), t-butyldimethylsilyl chloride (578 mg, 3.84 mmol), and imidazole (522 mg, 7.68 mmol) were stirred in 10 mL of dry DMF for 18 h at room temperature, water was added, and the reaction mixture was extracted several times with ethyl acetate. The combined organic layers were washed with 10% HCl solution, $NaHCO_3$ and NaCl solutions, dried ($Na_2SO_4$), and evaporated to dryness under vacuum. The crude product was purified by chromatography (elution with 2% ethyl acetate-hexanes) to give 777 mg (89%) of compound (20): mp 72–73° C. (from hexanes-methanol); IR (KBr) 1568, 1164, 1055, 1035, 846 $cm^{-1}$; $^1H$ NMR (400 MHz, $CDCl_3$) δ 7.53 (d, J=8.6 Hz, 1H), 6.50 (d, J=8.6 Hz, 1H), 4.52 (m, 2H), 3.08 (dd, J=15.0, 4.7 Hz, 1H), 3.01 (dd, J=15.0, 4.5 Hz, 1H), 2.88 (dd, J=15.0, 4.1 Hz, 1H), 2.72 (dd, J=15.0, 4.0 Hz, 1H), 1.32 (s, 3H), 1.19 (s, 3H,), 1.02 (s, 9H), 0.21 (s, 3H) 0.20 (s, 3H); $^{13}C$ NMR (50 MHz, $CDCl_3$) δ 153.5 (C), 139.9 (C), 136.6 (CH), 128.2 (C), 119.4 (CH), 108.2 (C), 90.2 (C), 74.3 (CH), 74.0 (CH), 39.2 ($CH_2$), 27.9 ($CH_2$), 26.5 ($CH_3$), 25.8 (CH), ($CH_3$), 18.3 (C), −4.1 ($CH_3$), −4.2 ($CH_3$); mass spectrum, m/z (relative intensity, %) 460 ($M^+$, 100), 445 (19), 345 (79), 218 (37), 73 (52). Analysis calculated for $C_{19}H_{29}IO_3Si$: C, 49.56; H, 6.35; found: C, 49.13; H, 5.99.

g) Compound 21: (±)-1-[6α,7α-(Isopropylidenedioxy)-4-t-butyldimethylsilyloxy-5,6,7,8-tetrahydronaphthyl]-2-[6α',7α'-dihydroxy-5',6',7',8'-tetrahydronaphthyl]ethyne as Two (±) Pairs.

Dichlorobis(triphenylphosphine)palladium(II) (31 mg, 5 mol %) and copper(I) iodide (4 mg, 2.5 mol %) were added to a solution of compound (20) (403 mg, 0.87 mmol) and compound (18) (165 mg, 0.87 mmol) in 12 mL of a 1:1 mixture of dry 1,4-dioxane and triethylamine. The mixture was refluxed for 21 h, diluted with water, acidified with 10% HCl, and extracted with ethyl acetate. The combined ethyl acetate layers were washed with NaCl solution, dried ($Na_2SO_4$), evaporated in vacuo, and chromatographed (elution with 50–100% ethyl acetate-hexanes) to yield 247 mg (54%) of compound (21) as a solid foam. The inseparable mixture of two (±) pairs had: IR (film) 3328, 1583, 1052, 1005 $cm^{-1}$; $^1H$ NMR (400 MHz, $CDCl_3$) δ 7.37 (d, J=7.4 Hz, 1H), 7.31 (d, J=8.3 Hz, 1H), 7.12 (t, J=7.6 Hz, 1H), 7.06 (d, J=7.6 Hz, 1H), 6.71 (d, J=8.4 Hz, 1H), 4.54 (m, 2H), 4.17 (m, 2H), 3.34–3.14 (m, 3H), 3.10–2.92 (m, 4H), 2.80 (ddd, J=15.0, 13.0, 4.5 Hz, 1H), 2.43 (br s, 1H, OH), 2.30 (br s, 1H, OH), 1.34 (s, 3H), 1.25 (s, 3H), 1.03 (s, 9H), 0.24 (s, 6H); $^{13}$C NMR (100 MHz, CDCl$_3$) δ 153.4 (C), 139.1 (C), 134.8 (C), 133.2 (C), 130.6 (CH), 130.5 (CH), 129.9 (CH), 129.7 (CH), 128.9 (CH), 126.4 (C), 126.0 (CH), 123.6 (C), 117.3 (CH), 115.5 (CH), 108.3 (C), 93.3 (C), 90.1 (C), 74.1 (CH), 74.0 (CH), 73.8 (CH), 69.2 (CH), 69.0 (CH), 68.9 (CH), 34.5 (CH$_2$), 33.7 (CH$_2$), 32.5 (CH$_2$), 29.7 (CH$_2$), 27.2 (CH$_2$), 27.1 (CH$_2$), 26.7 (CH$_3$), 26.6 (CH$_3$), 25.8 (CH$_3$), 24.5 (CH$_3$), 18.3 (C), −4.1 (CH$_3$), −4.2 (CH$_3$).; mass spectrum, m/z (relative intensity, %) 520 (M$^+$, 68), 502 (32), 484 (13), 73 (100). Exact mass calculated for C$_{31}$H$_{40}$O$_5$Si: 520.2645; found: 520.2615.

h) Compound 22: (E)-(±)-1,2-Bis[6α,7α-(Isopropylidenedioxy)-4-t-butyldimethylsilyloxy-5,6,7,8-tetrahydronaphthyl] ethene and its Meso Isomer Compound (20) (1.489 g, 3.23 mmol was dissolved in dry dioxane (3 mL). E-1,2-bis(tri-n-butylstannyl)ethylene (985 mg, 1.62 mmol) was added in 1 mL of dry dioxane, followed by tetrakis(triphenylphosphine)palladium(0) (198 mg, 0.16 mmol, 5 mol %), lithium chloride (413 mg, 9.7 mmol), and 2,6-di-t-butyl-4-methylphenol (a few crystals) in 20 mL of dry dioxane. A further portion of dry dioxane (10 mL) was added and the resulting solution was refluxed under nitrogen for 4 days. Several additional portions (total 2.5 mol %) of tetrakis(triphenylphosphine)palladium(0) were added during this time. The reaction mixture was cooled to room temperature, diluted with ether (200 mL), washed five times with 5% ammonium hydroxide solution. The aqueous layers were extracted three times with ether and the combined organic layers were dried (MgSO$_4$), filtered, and concentrated in vacuo. The crude product was chromatographed (elution with 0–5% ethyl acetate-hexanes) to afford 153 mg (14%) of compound (22) as a clear colourless oil: IR (neat): 1593, 1486, 1277, 1163, 1037 cm$^{-1}$; $^1$H NMR (400 MHz, CDCl$_3$) δ 7.37 (d, J=8.6 Hz, 1H), 7.13 (s, 1H), 6.73 (d, J=8.5 Hz, 1H), 4.49 (m, 2H), 2.96 (m, 4H), 1.34 (s, 3H), 1.27 (s, 3H), 1.05 (s, 9H,), 0.25 (s, 6H); $^{13}$C NMR (100 MHz, CDCl$_3$) δ 152.6 (C), 135.0 (C), 130.1 (C), 126.8 (CH), 126.2 (C), 124.7 (CH), 117.6 (CH), 108.4 (C), 74.5 (CH), 74.0 (CH), 30.5 (CH$_2$), 27.5 (CH$_2$), 26.9 (CH$_3$), 26.1 (CH$_3$), 24.8 (CH$_3$), 18.5 (C), −3.8 (CH$_3$), −3.9 (CH$_3$); mass spectrum, m/z (relative intensity, %) 692 (M$^+$, <1), 635 (1), 277 (44), 73 (100). Exact mass calculated for C$_{40}$H$_{60}$O$_6$Si$_2$: 692.3929; found: 692.3943.

i) Compound 24: 6,7-Isopropylidenedioxy-1,4-naphthoquinone

A mixture of diene [compound (23)]$^{25c}$ (1.030 g, 8.2 mmol), benzoquinone (2.65 g, 24.5 mmol), 2,6-di-t-butyl-4-methylphenol (57 mg) and benzene (10 mL) was heated in a sealed vessel under argon at 75–85° C. The mixture was concentrated and chromatographed (elution with 20% dichloromethane-hexanes) to give 1.25 g (66%) of compound (24): mp 195–198° C. (sealed capillary; dec.; from ethyl acetate); $^1$H NMR (200 MHz, CDCl$_3$) δ 7.35 (s, 2H), 6.84 (s, 2H), 1.73 (s, 6H); $^{13}$C NMR (50 MHz, CDCl$_3$) δ 184.0, 152.1, 138.0, 128.7, 120.7, 105.7, 25.9; mass spectrum, m/z (relative intensity, %) 230 (M$^+$, 100), 216 (24), 190 (51), 162 (23). Analysis calcd for C$_{13}$H$_{10}$O$_4$: C, 67.82; H, 4.38. Found: C, 67.45; H, 4.69.

j) Compound 25: 1-t-Butyldimethylsilyloxy-6,7-isopropylidenedioxy-4-trifloxynaphthalene A mixture of compound (24) (517 mg, 2.25 mmol) and 10% palladium on charcoal (9 mg) in ethyl acetate was stirred under hydrogen (balloon) for 2 h. The mixture was filtered and the filtrate was evaporated in vacuo. The resulting crude naphthol was dissolved in 20 mL of dry dichloromethane containing triethylamine (0.476 mL, 3.44 mmol) and t-butyldimethylsilyl chloride (371 mg, 2.47 mmol) was added. The solution was stirred under argon for 16 h and was then evaporated and chromatographed (elution with 10% ethyl acetate-hexanes) to give 430 mg (55%) of the corresponding monosilyl ether.

The above product (430 mg, 1.24 mmol), triethylamine (0.257 mL, 1.85 mmol) and triflic anhydride (0.224 mL, 1.36 mmol) were stirred in 10 mL of dry dichloromethane for 30 min. The mixture was poured into water and extracted with several portions of dichloromethane. The combined extracts were dried (Na$_2$SO$_4$), evaporated and chromatographed elution with 5% ethyl acetate-hexanes) to give 455 mg [42% overall yield from compound (24)] of compound (25) as an oil: IR: 1720, 1602, 1465, 1202, 1134 cm$^{-1}$; $^1$H NMR (200 MHz, CDCl$_3$) δ 7.43 (s, 1H), 7.21 (s, 1H), 7.16 (d, J=8.5 Hz, 1H), 6.68 (d, J=8.5 Hz, 1H), 1.77 (s, 6H), 1.11 (s, 9H), 0.32 (s, 6H); $^{13}$C NMR(50 MHz, CDCl$_3$) 6150.8, 149.5, 148.4, 139.0, 125.5, 124.7, 119.0, 118.7 (q, J=320 Hz), 116.1, 109.8, 99.5, 97.3, 26.0, 25.8, 18.4, −4.3; mass spectrum, m/z (relative intensity, 5%) 478 (M$^+$, 34), 347 (31), 346 (54), 345 (78), 73 (100). Exact mass calculated for C$_{20}$H$_{25}$F$_3$O$_6$SSi: 478.1093; found: 478.1129.

k) Compound 26: (E)-1,2-Bis[4-t-butyldimethylsilyloxy-6,7-(isopropylidenedioxy)-naphthyl]ethene A mixture of compound (25) (452 mg, 0.95 mmol), (E)-1,2-bis(tri-n-butylstannyl) ethylene (287 mg, 0.47 mmol), Pd(PPh)$_4$ (109 mg, 0.094 mmol) and LiCl (120 mg, 2.8 mmol) in dry dioxane (10 mL) was refluxed under argon for 4 days. After cooling, the mixture was diluted with hexanes and filtered. The filtrate was evaporated and chromatographed (elution with 1% ethyl acetate-hexanes) to give 298 mg of crude compound (26) containing ca 10% of starting material [compound (25)]. Further purification by preparative TLC (silica-gel, 2% ethyl acetate-hexanes) afforded 83% of pure compound (26) as an oil: IR: 1715, 1595, 1451, 1360, 1223, 1014, 960 cm$^{-1}$, $^1$H NMR (200 MHz, CDCl$_3$) δ 7.51 (s, 1H), 7.48 (d, J=8.0 Hz, 1H), 7.45 (s, 1H), 7.40 (s, 1H), 6.78 (d, J=8.0 Hz, 1H), 1.74 (s, 6H), 1.11 (s, 9H), 0.32 (s, 6H); $^{13}$C NMR (50 MHz, CDCl$_3$) δ 150.8, 148.3, 147.1, 129.8, 128.1, 127.3, 124.3, 122.3, 118.0, 111.4, 100.4, 99.4, 26.0, 25.9, 18.5, −4.1; mass spectrum, m/z (relative intensity, %) 684 (M$^+$, <1), 627 (12), 570 (16), 569 (23), 285 (23), 73 (100). Exact mass calculated for C$_{40}$H$_{52}$O$_6$Si$_2$: 684.3303; found: 684.3354.

l) Compound 28: (±)-4,4-(2,2-Dimethylpropylenedioxy)-2,3,4,4a,5,8,8a-hexahydro-1-naphthalenone 2,2-Dimethyl-1,3-propanediol (3.20 g, 30.8 mmol) and p-toluenesulfonic acid (117 mg, 0.615 mmol) were added to a solution of (cis-4a,8a)-2,3,4a,5,8,8a-hexahydro-1,4-naphthalenedione$^{26}$ [compound (27)] (10.1 g, 61.5 mmol) in 100 mL of benzene. The mixture was refluxed for 4 h in a flask equipped with a Dean Stark trap. The mixture was diluted with benzene, washed with NaHCO$_3$ solution, dried (MgSO$_4$), evaporated under reduced pressure, and chromatographed (elution with 8% ethyl acetate-hexanes) to provide two fractions. The first contained 6.82 g (89%, based on 2,2-dimethyl-1,3-propanediol as the limiting reagent) of a mixture of cis and trans isomers of compound (28) in the ratio of 20:80 with: IR (KBr) 1710, 1126, 1110, 757 cm$^{-1}$; $^1$H NMR (200 MHz, CDCl$_3$) δ 5.64 (m, 2H,), 3.76 (d, J=10.9 Hz, 1H), 3.65 (d, J=11.1 Hz, 1H), 3.50–3.35 (m, 2H), 3.07 (ddd, J=13.8, 5.4, 3.0 Hz, 1H), 2.66–2.15 (m, 7H), 1.95 (ddd, J=12.7, 10.4, 5.4 Hz, 1H), 1.50 (ddd, J=14.0, 14.0, 4.4 Hz, 1H), 1.24 (s, 2.4H, from trans-compound (28)), 1.06 (s, 0.6H, from cis- compound (28)), 0.98 (s, 0.6H, from cis-compound (28)), 0.78 (s, 2.4H, from trans- compound (28)); mass spectrum, m/z (relative intensity, %) 250 (M$^+$, 77), 193 (69), 107 (43), 79 (74), 69 (100). Analysis calculated for $C_{15}H_{22}O_3$: C, 71.97; H, +@ 8.86; found: C, 71.66; H, 8.80.

Further elution recovered 48% of partly epimerized starting material [compound (27)].

m) Compound 29a: (±)-trans-(4aα,8aβ)-4,4-(2,2-Dimethylpropylenedioxy)-6α,7α-dihydroxy-2,3,4,4a,5,6,7,8,8a-octahydro-1-naphthalenone and its trans-(4aα,8aβ)-6β,7β (compound 29b) and cis-(4aα,8aα)-6α,7α (compound 30) Isomers The 20:80 mixture of cis- and trans-compound (28) (3.60 g, 14.4 mmol) was dissolved in acetone and cooled to 0° C. Osmium tetroxide (1.84 mL of a 0.39 M solution in t-butanol), 4-methylmorpholine N-oxide (1.79 g, 15.3 mmol), and water (700 μL, 39 mmol) were added, and the mixture was stirred for 4 h before Florisil (5 g) and sodium thiosulfate (1 g) were added. The mixture was stirred overnight, filtered through Celite, evaporated in vacuo, and chromatographed (elution with 25–50% ethyl acetate-hexanes) to give 3.02 g (74%) of a mixture of the trans ring-fused isomers [compounds (29a) and (29b)] as a white powder and 0.34 g (8%) of the cis ring-fused isomer [compound (30)] as a white powder. The less polar trans isomers [compounds (29a) and (29b)] had: IR (KBr) 3381, 1713, 1101, 1022 cm$^{-1}$; $^1$H NMR (200 MHz, CDCl$_3$) δ 4.07 (br s, 1H), 3.77–3.57 (m, 3H), 3.47–3.35 (m, 2H), 3.10–2.97 (m, 1H), 2.52–2.25 (m, 3H), 2.19–1.93 (m, 3H), 1.83–1.41 (m, 3H), 1.21 (s, 3H), 0.77 (s, 3H); mass spectrum, m/z (relative intensity, %) 284 (M$^+$, 8) 227 (100), 141 (56). Exact mass calculated for $C_{15}H_{24}O_5$: 284.1624; found: 284.1609.

The more polar fraction contained the cis ring-fused isomer [compound (30)]: mp 137–138° C. (from ether); IR (KBr) 3457, 1714, 1118, 1110 cm$^{-1}$; $^1$H NMR (400 MHz, CDCl$_3$) δ 4.00 (br s, 1H), 3.87–3.85 (m, 1H), 3.70 (d, J=11.4 Hz, 1H), 3.55 (d, J=11.4 Hz, 1H), 3.49 (dd, J=11.4, 1.0 Hz, 1H), 3.43 (dd, J=11.4, 1.0 Hz, 1H), 3.13–3.10 (m, 1H), 2.89 (s, 1H), 2.59–2.50 (m, 2H), 2.44 (s, 1H) 2.33–2.17 (m, 3H), 2.01–1.96 (m, 1H), 1.85 (ddd, J=14.1, 14.1, 5.1 Hz, 1H), 1.55(ddd, J=12.1, 12.1,5.0 Hz, 1H), 1.17–1.09(m, 1H), 1.06 (s, 3H), 0.96(s, 3H); $^{13}$C NMR (50 MHz, CDCl$_3$) δ 211.6 (C), 97.7 (C), 70.1 (CH$_2$), 70.2 (CH$_2$), 68.7 (CH), 67.5 (CH), 44.9 (CH), 37.0 (CH$_2$), 34.0 (CH), 30.2 (C), 29.8 (CH$_2$), 29.3 (CH$_2$), 26.9 (CH$_2$), 22.8 (CH$_3$), 22.5 (CH$_3$); mass spectrum, m/z (relative intensity, %) 284 (M$^+$, 3) 227 (9), 141 (100). Exact mass calculated for $C_{15}H_{24}O_5$: 284.1624; found: 284.1618.

n) Compound 32: (±)-trans-(4aα,8aβ)-4,4-(2,2-Dimethylpropylenedioxy)-6α,7α-(isopropylidenedioxy)-2,3,4,4a,5,6,7,8,8a-octahydro-1-naphthalenone and its 6β,7β Isomer (compound 31)

The mixture of diols [compounds (29a) and (29b)] (3.9 g, 14 mmol), 2,2-dimethoxypropane (3.4 mL, 28 mmol), and p-toluenesulfonic acid (130 mg, 0.68 mmol) were refluxed in 200 mL of dichloromethane for 2 h. The reaction mixture was washed with NaHCO$_3$ solution, dried (MgSO$_4$), and concentrated in vacuo. The residue was purified by chromatography (elution with 5–10% ethyl acetate-hexanes) to give 1.8 g (40%) of compound (32) and 1.6 g (36%) of compound (31). Compound (32) had: mp 169–171° C. (from chloroform-hexanes); IR (KBr) 1710, 1218, 1098, 1055 cm$^{-1}$; $^1$H NMR (400 MHz, CDCl$_3$) δ 4.27 (br s, 1H), 4.01 (ddd, J=10.3, 5.1, 5.1 Hz, 1H), 3.72 (d, J=11.3 Hz, 1H), 3.70 (d, J=11.3 Hz, 1H), 3.43 (d, J=11.3 Hz, 1H), 3.37 (dd, J=11.3, 1.4 Hz, 1H), 3.02 (ddd, J=14.1, 5.1, 2.4 Hz, 1H), 2.57 (br d, J=13.0, 1H), 2.42 (ddd, J=14.5, 14.5, 5.6, 1H), 2.33 (m, 1H), 2.30–2.21 (m, 2H), 2.08–1.97 (m, 2H), 1.52–1.43 (m, 1H), 1.46 (s, 3H), 1.36 (m, 1H), 1.32 (s, 3H), 1.20 (s, 3H), 0.76 (s, 3H); $^{13}$C NMR (100 MHz, CDCl$_3$) δ 210.1 (C), 108.6 (C), 96.8 (C), 74.4 (CH), 73.5 (CH), 71.0 (CH$_2$), 70.2 (CH$_2$), 45.5 (CH), 45.0 (CH), 37.4 (CH$_2$), 30.4 (C), 29.3 (CH$_2$), 29.0 (CH$_3$), 26.9 (CH$_3$), 26.6 (CH$_2$), 26.1 (CH$_2$), 23.6 (CH$_3$), 22.5 (CH$_3$); mass spectrum, m/z (relative intensity, %) 324 (M$^+$, 35), 309 (56), 267 (91), 209 (11), 209 (37), 141 (100). Analysis calculated for $C_{18}H_{28}O_5$: C, 66.64; H, 8.70; found: C, 66.27; H, 8.33.

The more polar isomer [compound (31)] had: mp 131–132° C. (from chloroform-hexanes); IR (KBr) 1713, 1114,1093, 1042 cm$^{-1}$; $^1$H NMR (400 MHz, CDCl$_3$) δ 4.21 (ddd, J=4.2, 4.2, 1.9 Hz, 1H), 4.01 (ddd, J=10.5, 6.5, 4.6 Hz, 1H), 3.72 (d, J=11.3 Hz, 1H), 3.65 (d, J=11.3 Hz, 1H), 3.44 (dd, J=11.3, 2.6 Hz, 1H), 3.36 (dd, J=11.3, 2.6 Hz, 1H), 3.03 (ddd, J=14.1, 5.6, 2.8 Hz, 1H), 2.63 (ddd, J=12.2, 12.2, 4.0 Hz, 1H), 2.49–2.40 (m, 2H), 2.32–2.24 (m, 2H), 1.73 (ddd, J=12.7, 12.7, 10.7 Hz, 1H), 1.66 (ddd, J=16.0, 12.2,3.9 Hz, 1H), 1.54–1.47 (m, 1H), 1.51 (s, 3H), 1.40 (ddd, J=14.4, 14.4, 4.2 Hz, 1H), 1.32 (s, 3H), 1.20 (s, 3H), 0.74 (s, 3H); $^{13}$C NMR (100 MHz, CDCl$_3$) δ 210.9 (C), 108.6 (C), 96.5 (C), 74.8 (CH), 72.9 (CH), 71.0 (CH$_2$), 70.2 (CH$_2$), 48.1 (CH), 43.2 (CH), 37.5 (CH$_2$), 30.4 (C), 29.1 (CH$_3$), 28.5 (CH$_2$), 26.8 (2 CH$_2$), 26.3 (CH$_3$), 23.5 (CH$_3$), 21.7 (CH$_3$); mass spectrum, m/z (relative intensity, %) 324 (M$^+$, 2), 309 (19), 267 (100), 209 (11), 141 (86), 69 (80). Analysis calcd for $C_{18}H_{28}O_5$: C, 66.64; H, 8.70; found: C, 66.40; H, 9.11.

The cis ring-fused isomer [compound (30)], prepared as indicated above, was dissolved in 1 mL of methanol. To this solution, sodium methoxide (2 mL of a 0.13 M solution in methanol) was added and the mixture was refluxed for 2 h. It was then diluted with ethyl acetate, washed with NaHCO$_3$ solution, dried (Na$_2$SO$_4$), and evaporated in vacuo to give a quantitative yield of the epimerized acetonide [compound (32)] with properties identical to those of the preceding sample.

o) Compound 33: (±)-trans-(4aα,8aβ)-4,4-(2,2-Dimethylpropylenedioxy)-6α,7α-(isopropylidenedioxy)-1-trifloxy-4a,5,6,7,8,8a-hexahydro-(3H)-naphthalene

[Compound (32)] (2.27 g, 7.00 mmol) in 35 mL of dry THF was added dropwise to a solution of lithium diisopropylamide (85 mL of a 0.12 M solution in THF, 9.88 mmol) at −78° C., and stirring was continued for 3 h. N-Phenyltrifluoromethanesulfonimide (3.75 g, 10.5 mmol) in 30 mL of dry THF was slowly added and the mixture was allowed to warm to room temperature overnight. The reaction was quenched with water and the THF was removed on the rotary evaporator. The aqueous solution was extracted several times with hexanes, the combined extracts were washed with NaCl solution, dried (MgSO$_4$), and evaporated in vacuo. The crude product was subjected to Kugelrohr distillation, 80° C. at 0.1 Torr, to remove the last traces of the triflating agent. The distillation residue contained 2.4 g (75%) of compound (33) as a white solid: mp 132–133° C. (dec.) (from hexanes); IR (KBr) 1142, 1076, 1027, 910 cm$^{-1}$; $^1$H NMR (200 MHz, CDCl$_3$) δ 5.64–5.58 (m, 1H), 4.32 (m, 1H), 4.14–4.03 (m, 1H), 3.66 (d, J=11.5 Hz, 2H), 3.37 (d, J=11.6 Hz, 2H), 3.31–3.21 (m, 1H), 2.58 (d, J=13.2 Hz, 1H), 2.33–2.21 (m, 2H), 2.13–1.89 (m, 3H), 1.48 (s, 3H), 1.35 (s, 3H), 1.34–1.26 (m, 1H), 1.17 (s, 3H), 0.74 (s, 3H); $^{13}$C NMR (100 MHz, CDCl$_3$) δ 149.7 (C), 118.5 (q, J=320 Hz, CF$_3$) 114.7 (CH), 108.4 (C), 95.4 (C), 73.7 (CH), 73.3 (CH), 70.5 (CH$_2$), 70.3 (CH$_2$), 43.0 (CH), 36.7 (CH), 31.8 (CH$_2$), 30.0 (C), 28.6 (CH$_3$), 27.3 (CH$_2$), 26.4 (CH$_3$), 24.8 (CH$_2$), 22.9 (CH$_3$), 22.1 (CH$_3$); mass spectrum, m/z (relative intensity, %) 441 (M$^+$–15, 15), 323 (76), 265 (100). Analysis calculated for C$_{19}$H$_{27}$F$_3$O$_7$S: C, 50.00; H, 5.96; found: C, 50.01; H, 5.75.

p) Compound 34: (±)-1,2-Bis[trans-(4aα,8aβ)-4,4-(2,2-dimethylpropylene-dioxy)-6α,7α-(isopropylidenedioxy)-4a,5,6,7,8,8a-hexahydro-(3H)-naphthyl]ethyne and its Meso Isomer A solution of compound (33) (218 mg, 0.478 mmol) and bis(tri-n-butylstannyl)acetylene (144 mg, 0.238 mmol) in 6 mL of dry THF was added to a slurry of lithium chloride (61 mg, 1.4 mmol) and tetrakis(triphenylphosphine)palladium (0) (28 mg, 5 mol %) in 2 mL of THF. The mixture was refluxed for 12 h and was extracted several times with ether. The combined ether layers were washed twice with NaCl solution, dried (MgSO$_4$), and the solvent was evaporated. The crude product was chromatographed (elution with 7.5% ethyl acetate-hexanes) to afford 135 mg (89%) of an inseparable mixture of (±) and meso-compound (34): mp 295–296° C. (dec.) (from ethyl acetate); IR (KBr) 1151, 1133, 1120, 1110, 1096, 1048, 1021 cm$^{-1}$; $^1$H NMR (400 MHz, CDCl$_3$) δ 5.94 (m, 1H), 4.32 (br s, 1H), 4.11 (m, 1H), 3.68 (d, J=11.3 Hz, 1H), 3.63 (d, J=11.6 Hz, 1H), 3.33 (d, J=11.6 Hz, 2H), 3.22 (m, 1H), 2.59 (d, J=13.9 Hz, 1H), 2.46 (m, 1H), 2.05–1.99 (m, 2H), 1.84 (m, 2H), 1.48 (s, 3H), 1.35 (s, 3H), 1.29–1.27 (m, 1H), 1.18 (s, 3H), 0.73 (s, 3H); $^{13}$C NMR (100 MHz, CDCl$_3$) δ 130.6 (CH), 124.3 (C), 108.1 (C), 96.2 (C), 88.9 (C), 74.7 (CH), 73.8 (CH), 70.2 (CH$_2$), 70.1 (CH$_2$), 42.0 (CH), 37.3 (CH), 34.9 (CH$_2$), 30.0 (C), 29.3 (CH$_2$), 28.6 (CH$_3$), 26.6 (CH$_3$), 24.9 (CH$_2$), 23.0 (CH$_3$), 22.1 (CH$_3$); mass spectrum, m/z (relative intensity, %) 638 (M$^+$, 38), 580 (3), 552 (3), 267 (24), 83 (100). Analysis calculated for C$_{38}$H$_{54}$O$_8$: C, 71.44; H, 8.52; found: C, 71.12; H, 8.36.

q) Compound 35: (±)-(E)-1,2-Bis[trans-(4aα,8aβ)-4,4-(2,2-dimethylpropylenedioxy)-6α,7α-(isopropylidene-dioxy)-4a,5,6,7,8,8a-hexahydro-(3H)-naphthyl]ethene and its Meso Isomer Compound (33) (136 mg, 0.300 mmol) was converted into the coupled compound (35) by the same procedure used in the preparation of compound (34) except that (E)-1,2-bis (tri-n-butylstannyl)ethylene was used instead of bis(tri-n-butylstannyl)acetylene. Chromatography (elution with 7.5% ethyl acetate-hexanes) provided 85 mg (89%) of compound (35)as an inseparable mixture of (±)- and meso-compound (35): mp 312–315° C. (dec.) (from ethyl acetate-hexanes); IR (KBr) 1150, 1131, 1117, 1093, 1072, 1047,972 cm$^{-1}$; $^1$H NMR (400 MHz, CDCl$_3$) δ 5.95 (s, 0.5H, one diastereomer), 5.91 (s, 0.5H, other diastereomer), 5.55 (dd, J=16.1, 6.1 Hz, 1H), 4.35 (br s, 1H), 4.11 (m, 1H), 3.69 (d, J=11.3 Hz, 1H), 3.62 (d, J=11.6 Hz, 0.5H, one diastereomer), 3.58 (d, J=11.6 Hz, 0.5H, other diastereomer), 3.36–3.28 (m, 2H), 3.19 (dd, J=18.2, 6.3 Hz, 1H), 2.68–2.57 (m, 1H), 2.37 (m, 1H), 2.18–2.08 (m, 1H), 2.01 (d, J=18.3 Hz, 1H), 1.94–1.84 (m, 2H), 1.46 (s, 3H), 1.34 (s, 3H), 1.30–1.20 (m, 1H), 1.17 (s, 3H), 0.73 (s, 1.5H, one diastereomer), 0.72 (s, 1.5H, other diastereomer); $^{13}$C NMR (100 MHz, CDCl$_3$) δ 138.5 (CH), 138.4 (CH), 128.0 (CH), 127.8 (C), 122.3 (C), 122.2 (C), 108.0 (C), 96.5 (C), 74.9 (CH), 73.8 (CH), 70.3 (CH$_2$), 70.2 (CH$_2$), 42.9 (CH), 36.6 (CH), 36.4 (CH), 35.5 (CH$_2$), 35.4 (CH$_2$), 30.0 (C), 29.7 (C), 29.0 (CH$_2$), 28.6 (CH$_3$), 26.6 (CH$_3$), 26.5 (CH$_3$), 25.4 (CH$_2$), 23.0 (CH$_3$), 22.1 (CH$_3$); mass spectrum, m/z (relative intensity, %) 640 (M$^+$, 14), 267 (10), 141 (10), 83 (100). Exact mass calculated for C$_{38}$H$_{56}$O$_8$: 640.3975; found: 640.3978.

r) Compound 37: (±)-trans-(4aα,8aβ)-6α,7α-dihydroxy-2,3,4a,5,6,7,8a-octahydro-1,4-naphthalenedione A solution of compound (36)29 (1.12 g, 6.82 mmol), osmium tetroxide (870 μL of a 0.39 M 8 solution in t-butanol, 0.34 mmol), 4-methylmorpholine N-oxide (840 mg, 7.17 mmol), and water (0.25 mL, 14 mmol) was stirred for 3 h. Florisil (2.5 g) and sodium thiosulfate (0.5 g) were added, and the mixture was stirred for a further 1 h. The solid material was removed by filtration, the solvent was evaporated in vacuo, and the crude product was purified by 4: chromatography (elution with 70–100% ethyl acetate-hexanes) to afford 1.2 g (89%) of compound (37)-as a solid foam: IR (KBr) 3442, 1709, 1156, 1061, 1008 cm$^{-1}$: $^1$H NMR (200 MHz, acetone-d$_6$-CD$_3$OD) δ 4.03–3.88 (m, 1H), 3.55 (d, J=12.0, 4.6, 2.7 Hz, 1H), 2.88–2.45 (6H), 2.25 (dt, J=14.4, 3.8 Hz, 1H), 2.05 (dt, J=8.2, 3.8, Hz, 1H), 1.72 (m, 1H), 1.50 (ddd, J=14.2, 11.9, 2.3 Hz, 1H); $^{13}$C NMR (50 MHz, CD$_3$COCD$_3$—CD$_3$OD) δ 210.8 (C), 209.6 (C), 71.2 (CH), 68.8 (CH), 47.9 (CH), 43.5 (CH), 37.3 (CH$_2$), 37.2 (CH$_2$), 32.1 (CH$_2$), 28.9 (CH$_2$); mass spectrum, m/z (relative intensity, %) 198 (M$^+$, 11), 180 (53), 151 (55), 95 (85), 81 (100). Exact mass calcd for C$_{10}$H$_{14}$O$_4$: 198.0892; found: 198.0881.

C. Synthesis of Mimetics a) Mimetic 3: (±)-1,2-Bis[4,6α,7α-trihydroxy-5,6,7,8-tetrahydronaphthyl]ethyne and its Meso Isomer Compound (19) (257 mg, 0.556 mmol) was stirred in 10 mL of 80% acetic acid solution at 60° C. for 1 h and then the acetic acid was removed in vacuo. The residue was purified by chromatography (elution with 5% ethanol-chloroform) to furnish 101 mg (47%) of mimetic (3) as an inseparable mixture of (±)- and meso-diastereomers: mp 280–283° C. (from methanol-water); IR (KBr) 3390, 1582, 1062, 812 cm$^{-1}$; $^1$H NMR (400 MHz, CD$_3$OD) δ 7.16 (d, J=8.3 Hz, 1H), 6.60 (d, J=8.3 Hz, 1H), 4.08 (m, 2H), 3.14 (d, J=5.5 Hz, 2H), 2.87 (d, J=5.6 Hz, 2H); $^{13}$C NMR (100 MHz, CD$_3$OD) δ 156.7 (C), 138.2 (C), 131.5 (CH,), 122.6 (C), 115.9 (C), 113.1 (CH), 92.3 (C), 70.3 (CH), 69.9 (CH), 35.0 (CH$_2$), 30.2 (CH$_2$); mass spectrum, m/z (relative intensity, %) 382 (M$^+$, 2), 99 (11), 69 (11), 40 (100). Analysis calcd for C$_{22}$H$_{22}$O$_6$: C, 69.10; H, 5.80; found: C, 68.79; H, 6.03.

b) Mimetic 4: (±)-1-[4,6α,7α-Trihydroxy-5,6,7,8-tetrahydronaphthyl]-2-[6α',7α∝-dihydroxy-5',6',7',8'-tetrahydronaphthyl]ethyne as Two (±) Pairs Compound (21) (200 mg, 0.38 mmol) was dissolved in 15 mL of THF, cooled to 0° C., and tetra-n-butylammonium fluoride (420 μL of a 1 M solution in THF, 0.42 mmol) was added. After 2 h, NH$_4$Cl solution was added and the reaction mixture was extracted several times with ethyl acetate. The extracts were washed with NaCl solution, dried (Na$_2$SO$_4$), evaporated under reduced pressure, and chromatographed (elution with 100% ethyl acetate) to furnish 143 mg (92%) of the corresponding phenol, which was used directly in the next step.

The above phenol (143 mg, 0.352 mmol) was stirred in 5 mL of 80% acetic acid solution for 45 min at room temperature. The solvent was removed in vacuo and the solid residue was repeatedly dissolved in methanol and evaporated under reduced pressure to remove the final traces of acetic acid. This afforded 117 mg (91%) of mimetic (4), obtained as an inseparable mixture of two (±) pairs. It was further purified by recrystallization from methanol: mp 278–281° C.; IR (KBr) 3360, 1580, 1073 cm$^{-1}$; $^1$H NMR (400 MHz, CD$_3$OD) δ 7.30 (d, J=7.2 Hz, 1H), 7.21 (d, J=8.2 Hz, 1H), 7.09 (m, 2H), 6.62 (d, J=8.2 Hz, 1H), 4.14–4.07 (m, 4H), 3.17 (m, 4H), 2.99 (m, 2H), 2.87 (m, 2H); $^{13}$C NMR (100 MHz, CD$_3$OD) δ 154.9 (C), 136.4 (C), 134.4 (C), 133.2 (C), 130.0 (CH), 128.7 (CH), 128.0 (CH), 125.0 (CH), 123.1 (C), 120.5 (C), D 113.2 (C), 111.3 (CH), 92.7 (C), 89.8 (C), 68.3 (CH), 68.2 (CH), 68.1 (CH), 67.8 (CH), 33.7 (CH$_2$), 32.9 (CH$_2$), 32.8 (CH$_2$), 28.2 (CH$_2$); mass spectrum, m/z (relative intensity, %) 366 (M⁺, 39), 348 (7), 330 (14), 83 (32), 40 (100). Exact mass calculated for $C_{22}H_{22}O_5$: 366.1467; found: 366.1450.

c) Mimetic 5: (±)-1,2-Bis[6α,7α-dihydroxy-5,6,7,8-tetrahydronaphthyl]ethyne and its Meso Isomer Compound (17) (242 mg, 0.83 mmol) and compound (18) (157 mg, 0.83 mmol) were dissolved in 6 mL of dry 1,4-dioxane and 6 mL of dry triethylamine. Dichlorobis-(triphenylphosphine)palladium(II) (29 mg, 5 mol %) and copper(I) iodide (4 mg, 2.5 mol %) were added and the reaction was refluxed for 24 h. The mixture was diluted with water, filtered, and the filtrate was evaporated under reduced pressure. Chromatography with 5–10% methanol-chloroform gave 125 mg (43%) of mimetic (5) as a tan powder consisting of an inseparable mixture of (±)-and meso-diastereomers: IR (KBr) 3341, 1582, 1206, 1174, 1080 cm⁻¹; ¹H NMR (400 MHz, CD₃OD) δ 7.35 (dd, J=7.2, 1.8 Hz, 1H), 7.13 (m, 2H), 4.12 (ddd, J=6.8, 5.3, 1.8 Hz, 1H), 4.08 (ddd, J=6.4, 5.1, 2.0 Hz, 1H), 3.26–3.14 (m, 2H), 3.06–2.95 (m, 2H); ¹³C NMR (100 MHz, CD₃OD) δ 137.0 (C), 135.8 (C), 130.9 (CH), 130.6 (CH), 127.1 (CH), 124.6 (C), 93.9 (C), 70.3 (CH), 70.1 (CH), 35.7 (CH₂), 35.0 (CH₂); mass spectrum, m/z (relative intensity, 5%) 350 (M⁺, 100), 314 (60), 296 (26), 215 (27). Exact mass calculated for $C_{22}H_{22}O_4$: 350.1518; found: 350.1502.

d) Mimetic 6: (E)-(±)-1,2-Bis[4,6α,7α-trihydroxy-5,6,7,8-tetrahydronaphthyl]ethene and its Meso Isomer Compound (22) (204 mg, 0.295 mmol) was dissolved in dry THF (22 mL) at 0° C. and tetra-n-butylammonium fluoride in THF (1 M, 0.6 mL, 0.6 mmol) was added under argon and the solution was stirred for 10 min. Saturated NH₄Cl solution was added and the mixture was stirred for an additional 10 min. It was then extracted four times with ethyl acetate, the organic layers were combined and washed with brine, dried (MgSO₄), filtered, and concentrated in vacuo to afford a white solid. The crude product was chromatographed (elution 0–80% ethyl acetate in hexanes) to give 122 mg (89%) of the corresponding bisphenol; mp 233–238° C.; IR (KBr) 3344, 1592, 1377, 1281, 1156, 1048 cm⁻¹; ¹H NMR (400 MHz, DMSO-d₆) δ 9.26 (s, 1H), 7.37 (d, J=8.6 Hz, 1H), 7.06 (s, 1H), 6.70 (d, J=8.5 Hz, 1H), 4.50 (m, 2H), 3.00 (m, 1H), 2.92 (m, 1H), 2.70 (m, 1H), 2.55 (m, 1H), 1.22 (s, 3H), 1.03 (s, 3H); ¹³C (100 MHz, DMSO-d₆) δ 153.6 (C), 134.4 (C), 127.2 (CH), 124.6 (CH), 123.7 (CH), 121.3 (C), 113.1 (CH), 106.9 (C), 73.5 (CH), 72.9 (CH), 29.0 (CH₂), 26.4 (CH₃), 25.7 (CH₂), 24.3 (CH₃); mass spectrum, m/z (relative intensity, %) 464 (M⁺, 5), 406 (29), 348 (100). Exact mass calculated for $C_{28}H_{32}O_6$: 464.2199; found: 464.2205.

The above product (109 mg, 0.228 mmol) was stirred in 5 mL of 80% acetic acid for 1 h. at 60° C. The solvent was evaporated in vacuo to afford a yellow solid that was triturated with 3 mL of 50% methanol-chloroform, filtered and dried to afford mimetic (6) (68 mg, 76%) as a white crystalline solid; mp>310° C., IR (KBr) 3329, 1587, 1458, 1282, 1067 cm⁻¹; ¹H NMR (400 MHz, DMSO-d₆) δ 9.23 (s, 1H), 7.25 (d, J=8.4 Hz, 1H), 6.90 (s, 1H), 6.63 (d, J=8.3 Hz, 1H), 4.54 (dd, J=13.0, 3.3 Hz, 2H), 3.86 (m, 2H), 2.82 (m, 2H), 2.66 (d, J=5.2 Hz, 2H); ¹³C NMR (100 MHz, DMSO-d₆) δ 154.4 (C), 133.2 (C), 127.5 (C), 124.8 (CH), 123.3 (CH), 121.3 (C), 112.0 (CH), 68.1 (CH), 67.4 (CH), 32.4 (CH₂), 29.4 (CH₂).

e) Mimetic 7: (E)-(±)-1,2-Bis[6α,7α-dihydroxy-5,6,7,8-tetrahydronaphthyl]ethene and its Meso Isomer Compound (17) (217 mg, 0.748 mmol) and E-1,2-bis(tri-n-butylstannyl)ethylene (235 mg, 0.374 mmol) were dissolved in 2 mL of dry dioxane. A solution of lithium chloride (100 mg, 2.38 mmol), tetrakis(triphenylphosphine) palladium(0) (50 mg, 0.043 mmol), and 2,6-di-t-butyl-4-methylphenol (a few crystals) in 4 mL of dry dioxane was added. The mixture was refluxed under nitrogen for 48 h. After 24 h, another portion of 100 mg of tetrakis (triphenylphosphine)palladium(0) was added. The reaction mixture was then diluted with water (10 mL) and 10 mL of 10% isopropanol-chloroform. The aqueous layer was extracted repeatedly with 10% isopropanol-chloroform and the combined organic layers were washed with brine, dried (MgSO₄) and concentrated in vacuo to afford a white solid. The crude product was chromatographed (elution 0–15% methanol-chloroform) to afford 27 mg (19%) of mimetic (7) as white crystals; mp 260–263° C. (from methanol); IR (KBr) 3344, 1676, 1456, 1057 cm⁻¹; ¹H NMR (400 MHz, DMSO-d₆) δ 7.44 (d, J=7.9 Hz, 1H), 7.17 (s, 1H), 7.13 (t, J=7.7 Hz, 1H), 7.00 (d, J=7.7 Hz, 1H), 4.65 (d, J=3.8 Hz, 1H), 4.62 (d, J=4.5 Hz, 1H), 3.91 (m, 2H), 2.89 (m, 4H); ¹³C NMR (400 MHz, DMSO-d₆) δ 136.2 (C), 134.8 (C), 132.3 (C), 128.4 (CH), 127.7 (CH), 125.7 (CH), 123.1 (CH), 68.1 (CH), 67.7 (CH), 34.9 (CH₂), 32.4 (CH₂); mass spectrum, m/z (relative intensity, %) 352 (M⁺, 59), 221 (67), 115 (79), 60 (100), 43 (67). Exact mass calcd for $C_{22}H_{24}O_4$: 352.1675; found: 352.1671.

f) Mimetic 8: (±)-1,2-Bis[4,6α,7α-trihydroxy-5,6,7,8-tetrahydronaphthyl]ethane and its Meso Isomer Compound (22) (152 mg, 0.219 mmol) was dissolved in 8 mL of ethyl acetate. Palladium on charcoal (2.4 mg of 10%) was added and the mixture was stirred vigorously at room temperature under 1 atm of hydrogen (balloon) overnight. The mixture was filtered through Celite and concentrated in vacuo to afford the reduced product (144 mg, 95%) as a clear, colourless oil: IR (neat) 1596, 1486, 1268, 1057, 841 cm⁻¹; ¹H NMR (200 MHz, CDCl₃) δ 6.81 (dd, J=8.4, 5.1 Hz, 1H), 6.60 (dd, J=8.3, 2.2 Hz, 1H), 4.34 (m, 2H), 3.04–2.71 (m, 6H), 1.33 (s, 3H), 1.28 (s, 3H), 1.02 (s, 9H), 0.20 (s, 6H); ¹³C NMR (50 MHz, CDCl₃) δ 151.3 (C), 135.2 (C), 132.3 (C), 128.0 (CH), 126.1 (C), 117.0 (CH), 108.4 (C), 74.5 (CH), 74.1 (CH), 34.8 (CH₂), 30.6 (CH₂), 27.6 (CH₂), 26.9 (CH₃), 26.1 (CH₃), 24.7 (CH₃), 18.5 (C), −3.9 (CH₃), −3.9 (CH₃); mass spectrum, m/z (relative intensity, %) 694 (M⁺, <1), 561 (10), 347 (100). Exact mass calculated for $C_{40}H_{62}O_6Si_2$: 694.4085; found 694.4069.

The above product (318 mg, 0.457 mmol) was dissolved in 35 mL of dry THF at 0° C. Tetra-n-butylammonium fluoride (1 mL of a 1 M solution in THF, 1 mmol) was added and the reaction mixture was stirred at 0° C. for 10 min. Saturated ammonium chloride solution was added and the mixture was stirred for 15 min. The mixture was then extracted four times with ethyl acetate, the organic layers were combined and washed with brine, dried (MgSO₄) and concentrated in vacuo. The crude material was chromatographed (elution with 0–80% ethyl acetate-hexanes) to afford 184 mg (86%) of the desilylated product; mp 210–215° C.: IR (KBr) 3332, 1596, 1495, 1283, 1209, 1159, 1046 cm⁻¹; ¹H NMR (400 MHz, DMSO-d₆) δ 8.92 (d, J=3.7 Hz, 1H), 6.73 (dd, J=8.2, 1.3 Hz, 1H), 6.55 (d, J=8.2 Hz, 1H), 4.43 (s, 2H), 2.90–2.50 (m, 6H), 1.22 (s, 3H), 1.03 (s, 3H); ¹³C NMR (400 MHz, DMSO-d₆) δ 152.3 (C), 134.4 (C), 129.6 (C), 127.1 (CH), 121.3 (C), 112.5 (CH), 106.9 (C), 73.5 (CH), 73.0 (CH), 34.4 (CH₂), 29.4 (CH₂), 26.4 (CH₃), 25.9 (CH₂), 24.4 (CH₃); mass spectrum, m/z (relative intensity, %) 466 (M⁺, 1), 233 (29), 175 (81), 128 (100). Exact mass calculated for $C_{28}H_{34}O_6$: 466.2355; found: 466.2387.

The diacetonide (110 mg, 0.235 mmol) was stirred in 6 mL of 80% acetic acid at 60° C. for 2 h. The solvent was evaporated in vacuo to afford a pale yellow solid. The crude product was triturated with 5 mL of 50% chloroform-methanol solution to afford 70 mg (77%) of compound (8) as a white crystalline solid; mp>315° C.: IR (KBr) 3298, 1589, 1458, 1283, 1062 cm$^{-1}$; $^1$H NMR (400 MHz, DMSO-d$_6$) δ 8.90 (s, 1H), 6.80 (d, J=8.1 Hz, 1H), 6.55 (d, J=8.1 Hz, 1H), 4.51 (m, 2H), 3.85 (s, 2H), 2.76 (m, 2H), 2.66 (m, 2H), 2.54(s, 2H); $^{13}$C NMR (100 MHz, DMSO-d$_6$) δ 153.0 (C), 133.3 (C), 130.0 (C), 126.1 (CH), 121.3 (C), 111.4 (CH), 68.2 (CM), 67.5 (CH), 33.2 (CH$_2$), 31.7 (CH$_2$), 29.6 (CH$_2$).

g) Mimetic 9: 1,2-Bis(4,6,7-trihydroxynaphthyl)ethane

Compound (26) (50 mg, 0.073 mmol) and 10% palladium on charcoal (12 mg) were stirred in ethyl acetate for 12 h under hydrogen (balloon). The mixture was filtered and evaporated to give 48 mg (96%) of the protected mimetic (9). This was refluxed in 15 mL of 80% acetic acid for 12 h. The solution was evaporated and the residue was chromatographed (elution with 50% ethyl acetate-hexanes, followed by 30% methanol-chloroform) to give 24 mg (91%) of -[compound (9)]-as an oil: IR: 3320, 1616, 1592, 1448, 1238, 1144 cm$^{-1}$; $^1$H NMR (200 MHz, acetone-d$_6$) δ 7.61 (s, 1H), 7.43 (s, 1H), 6.95 (d, J=7.5 Hz, 1H), 6.59 (d, J=7.5 Hz, 1H), 3.13 (s, 2H); $^{13}$C NMR (200 MHz, acetone-d$_6$) δ 151.0, 146.8, 145.3, 129.5, 128.1, 123.9, 121.4, 106.9, 106.1, 105.9, 34.6; mass spectrum, m/z (relative intensity, %) 378 (M$^+$, 1.7), 189 (39), 188 (100), 160 (95), 114 (71). Exact mass calcd for C$_{22}$H$_{18}$O$_6$: 378.1103; found: 378.1135.

h) Mimetic 10: (±)-1,2-Bis[trans-(4aα,8aβ)-4-oxo-6α,7α-dihydroxy-4a,5,6,7,8,8a-hexahydro -(3H)-naphthyl]ethyne and its Meso Isomer Compound (34) (100 mg, 0.156 mmol) was stirred in 50 mL of 80% acetic acid for 18 h. The 8 acetic acid was then removed by distillation at 0.1 Torr, while the temperature of the still pot was kept below 30° C. The remaining yellow powder was washed several times with benzene to remove 2,2-dimethyl-1,3-propanediol. The residue contained 32 mg (53%) of mimetic 10 as a mixture of (±) and meso isomers: mp>300° C.; IR (KBr) 3376, 1708, 1667, 1004 cm$^{-1}$; $^1$H NMR (400 MHz, DMSO-d$_6$) δ 6.13 (dd, J=6.5, 3.8 Hz, 1H), 4.54 (d, J=5.8 Hz, 1H), 4.34 (d, J=2.8 Hz, 1H), 3.80 (br s, 1H), 3.40–3.38 (m, 1H), 3.25–3.19 (m, 1H), 2.79 (d, J=22.7 Hz, 1H), 2.59–2.51 (m, 1H), 2.29–2.23 (m, 1H), 2.03 (ddd, J=12.1, 3.7, 3.7 Hz, 1H), 1.89 (ddd, J=14.2, 3.4, 3.4 Hz, 1H), 1.62 (dd, J=24.3, 12.1 Hz, 1H), 1.35 (dd, J=13.1, 13.1 Hz, 1H); $^{13}$C NMR (100 MHz, DMSO-d$_6$) δ 208.7 (C), 131.7 (CH), 124.3 (C), 88.7 (C), 70.1 (CH), 67.4 (CH), 44.8 (CH), 40.5 (CH$_2$), 39.9 (CH), 33.3 (CH$_2$), 29.9 (CH$_2$). Since mimetic (10) was insufficiently volatile to provide a satisfactory electron impact mass spectrum, it was converted to the corresponding hexaacetate by treatment with acetic anhydride in pyridine in the presence of a catalytic amount of 4-dimethylaminopyridine for 5 h. The hexaacetate had: $^1$H NMR (200 MHz, CDCl$_3$) δ 6.33 (dd, J=6.1, 2.8 Hz, 1H), 5.85 (dd, J=6.2, 2.7 Hz, 1H), 5.36 (br s, 1H), 4.92–4.81 (m, 1H), 2.83–2.73 (m, 1H), 2.52–2.20 (m, 3H), 2.18 (s, 3H), 2.10 (s, 3H), 2.04 (s, 3H), 2.02–1.82 (m, 1H), 1.77–1.59 (m, 2H); mass spectrum, m/z (relative intensity, %) 638 (M$^+$, 0.6), 596 (1), 554 (3), 43 (100). Exact mass calculated for C$_{34}$H$_{38}$O$_{12}$: 638.2363; found: 638.2330.

i) Mimetic 11: (E)-1,2-Bis[trans-(4aα,8aβ)-4-oxo-6α,7α-dihydroxy-4a,5,6,7,8,8a-hexahydro-(3H)-naphthyl]ethene and its Meso Isomer Compound (35) (100 mg, 0.156 mmol) was deprotected by stirring for 14 h in 50 mL of 80% acetic acid solution. The acetic acid was removed by distillation under high vacuum with the temperature of the still pot never exceeding 30° C. The yellow residue was triturated with chloroform to remove 2,2-dimethyl-1,3-propanediol. The residue contained 24 mg (40%) of mimetic (11) as a mixture of (±)- and meso-isomers: mp>300° C.; IR (KBr) 3386, 1706, 1658, 1072, 1010 cm$^{-1}$; $^1$H NMR (400 MHz, DMSO-d$_6$) δ 6.25 (m, 1H), 5.81 (m, 1H), 4.49 (d, J=5.7 Hz, 1H), 4.31 (d, J=3.1 Hz, 1H), 3.80 (br s, 1H), 3.42–3.39 (m, 1H), 3.23–3.12 (m, 1H), 2.73–2.68 (m, 1H), 2.63–2.57 (m, 1H), 2.35 (m, 1H), 1.98 (m, 1H), 1.88 (m, 1H), 1.56–1.45 (m, 1H), 1.41–1.34 (m, 1H); $^{13}$C NMR (100 MHz, DMSO-d$_6$) δ 210.8 (C), 139.8 (CH), 131.7 (CH), 121.8 (C), 71.3 (CH), 63.3 (CH), 45.7 (CH), 42.0 (CH), 41.4 (CH$_2$), 34.3 (CH$_2$), 31.0 (CH$_2$). Mimetic (11) was insufficiently volatile to provide a satisfactory electron impact mass spectrum and therefore was converted into its corresponding diacetonide by treatment with 2,2-dimethoxypropane and p-toluenesulfonic acid in methylene chloride for 2 h. This had: $^1$H NMR (200 MHz, CDCl$_3$) δ 6.21–6.05 (m, 1H), 5.91–5.71 (m, 1H), 4.43–4.27 (m, 1H), 4.24–4.01 (m, 1H), 3.32–3.08 (m, 1H), 2.97–2.61 (m, 2H), 2.57–2.14 (m, 4H), 1.95–1.80 (m, 1H), 1.51 (s, 3H), 1.37 (s, 3H); m/z (relative intensity, %) 468 (M$^+$, 3), 466 (11), 464 (14), 59 (49), 43 (100). Exact mass calculated for C$_{28}$H$_{36}$O$_6$: 468.2511; found: 468.2483.

j) Mimetic 12: 6,7-Dihydroxy-2,3,4a,5,6,7,8,8a-octahydro-4-oxo-naphthalenone Azine (Mixture of Isomers)

A solution of compound (37) (112 mg, 0.57 mmol) and hydrazine (8 μL of 55%, 0.1 mmol) was refluxed in 5 mL of n-butanol for 3 h before the n-butanol was removed by Kugelrohr distillation at 50° C. at 0.1 Torr. The crude product was purified by chromatography (elution with 5–15% methanol-chloroform) to give 71 mg (63%) of recovered starting material and 31 mg (40% based on hydrazine) of a mixture of azine stereoisomers [compound (12)] as a white powder. The mixture had: mp>300° C.; IR (KBr) 3428, 1710, 1634 cm$^{-1}$; $^1$H NMR (200 MHz, DMSO-d$_6$) δ 4.61–4.18 (m, 2H,), 3.79 (br s, 1H), 3.50–3.36 (m, 1H), 2.95–2.54 (m, 3H), 2.44–2.11 (m, 3H), 2.09–1.26 (m 4H); due to the complexity of the carbon spectrum only the distinguishing signals are listed: $^{13}$C NMR (50 MHz, CDCl$_3$—CD$_3$OD) δ 211.8–210.3 (m, C=O), 163.5–162.4 (m, C=N), 70.5–70.2 (m, C-6 or C-7), 67.7–66.9 (m, C-6 or C-7); mass spectrum, m/z (relative intensity, %) 392 (M$^+$, 4), 310 (5), 249 (5), 36 (100). Exact mass calculated for C$_{20}$H$_{28}$N$_2$O$_6$: 392.1947; found: 392.1942.

D. Bioassays

Mimetics 3–12, along with brassinolide as a standard, were tested for biological activity by means of the rice leaf lamina assay, using a dwarf rice *Oryza satina* var. Tanginbozu, as described[30]. The compounds were dissolved in 95% ethanol, except for mimetic 11 where DMSO was used due to poor solubility in ethanol. To a solution of mimetic 11 in 50 microliters of DMSO was added 550 microliters of a 2.5% aqueous solution of Atlas®, an ICI formulating material, to improve uptake. The test solutions were then applied as 0.5 μl microdrops to the rice plants 48 h after planting the germinated seeds on 0.8% water agar. At high doses, several rounds of application of the 0.5 μl microdrops were required to attain the desired dose per plant. Where IAA was a co-treatment, 1,000 or 5,000 ng of IAA was similarly applied per plant ca. 2 h prior to the application of brassinolide and mimetics 3–12. The resultant leaf lamina angle was measured 60–65 h later. For an individual bioassay, each data point is the mean of the leaf angles from ca. 36 plants for doses up to 100 ng and from ca. 24 plants for the 1000 and 10,000 ng doses. Parallel control applications of solvent and IAA (1000 ng) were also carried out. The results for inactive mimetics 5, 7, 8, 9, 10 and 12 are not shown. Similarly, the results for brassinolide plus IAA, which were reported earlier,[14,16,17a] are not shown here for purposes of clarity. Results for active mimetics 3, 4, 6 and 11 are given in FIGS. 8–11, respectively.

4. Formulations and Methods of Application

The compounds of the invention may be used either alone or in combination. They may be applied in combination with adjuvants such as spreading agents, wetting agents, dispersants, or binding agents, or admixed with agricultural additives such as insecticides, fungicides, herbicides, soil disinfectants, or fertilizers. The dosage form may be, for example, a liquid, suspension, emulsion, powder, wettable powder, granules, or tablets.

A preferred liquid vehicle is an aqueous solvent. Other liquid carriers that may be used include alcohols such as methanol, butanol and glycol, ketones such as acetone, hydrocarbons such as toluene, xylene and cyclohexane, amides such as dimethylformamide, sulfoxides such as dimethylsulfoxide, animal and vegetable oils, and fatty acids and their esters. A surfactant may be employed as an emulsifier or dispersing agent. Nonionic or anionic surfactants, such as polyethylene oxide derivatives, fatty acid esters, sodium alkyl sulfates, and quaternary ammonium salts, are commonly employed.

Solid carriers that may be used include, for example, clay, talc, diatomaceous earth, silica, calcium carbonate, bentonite, quartz, alumina, vermiculite, vegetable-based organic materials such as soybean powder, wheat flour, wood flour, starch and crystalline cellulose; polymeric substances such as alkyd resin, polyalkyleneglycol, ketone resin, ester gum, copal gum and dammar gum; and waxes such as carnauba wax and beeswax.

The compounds of the present invention should preferably be formulated with an appropriate formulating material, such as Atlas G-1086 (poloxyethylene sorbitol hexaoleate), a proprietary formulation of ICI Americas Inc., a subsidiary of Imperical Chemical Industries PLC.

It is also preferable to coapply the compounds of the present invention with a plant growth regulator such as an auxin, a cytokinin or a gibberellin. An auxin such as IAA has been found to be effective. The auxin may preferably be co-applied in ratios of about 1:1 to about 500,000:1 or higher (auxin:mimetic) with the mimetic.

Such formulations are prepared by means of standard procedures of agro chemical manufacture. The concentration of the active ingredients) in the formulation varies with the crop plant, type of formulation, method of application, treating time and period, and other conditions. When applied as a solution or dispersion in water or an organic solvent, a concentration of $10^{-5}$ ppm to 1000 ppm, and more preferably $10^{-3}$ ppm to 350 ppm of active ingredient, is preferable. The compounds of the invention may be effective in very small amounts per plant. The amount applied may generally vary between 1 picogram to 1 mg per plant, preferably about 0.1 to 1000 ng per plant, or 100 $\mu$g to 10 g per acre, preferably about 0.5 to 10 mg per acre. Higher or lower concentrations or dosages may be appropriate depending on the activity of the compound in the species being treated within the particular formulation made.

The appropriate treating area, treating method, and treating time or season are determined in accordance with standards known in the field. Effective methods of administration include immersion, prior to planting, of seedings, plantings or root plants, spraying of plant surfaces during the growth period, injection into plants, or application onto the soil. The application can be repeated as needed. For increasing the yield of cereal crops, the compounds are preferably applied at about the time of flowering; i.e., the period from the beginning of formation of reproductive cells to nearly the end of seed or fruit ripening.

The mimetics described herein may promote growth and development of higher plants and enhances the crop yield of horticultural, agricultural, floricultural and forestry plants as would be expected from the application of a brassinosteroid. Beneficial effects of the mimetics described herein include promoting a desired tissue morphology and/or physiological state in a higher plant wherein such desired tissue morphology or physiological state is promoted by a brassinosteroid. Such beneficial effects may include growth promotion, enhanced crop quality, and increased resistance to disease, herbicides, bactericides, insecticides, low temperature or high temperature stress, and moisture stress. Crops whose growth may be regulated include graminaceous crops (i.e. cereals) such as rice, wheat, corn, barley, or oats, fruit trees, beans, such as soy beans, coffee or cocoa, root crops, fruity vegetables, leafy vegetables, woody plants, and flowering plants.

5. REFERENCES

The following references are cited in the application as superscript numbers at the relevant portion of the application:

1. Grove, M. D.; Spencer, G. F.; Rohwedder, W. K.; Mandava, N.; Worley, J. F.; Warthen Jr., J. D.; Steffens, G. L.; Flippen-Anderson, J. L.; Cook Jr., J. C. *Nature* 1979, 281, 216–217.
2. (a) For a review, see: Back, T. G. In *Studies in Natural Products Chemistry*; Atta-ur-Rahman, Ed., Elsevier: Amsterdam, 1995, Vol. 16; pp. 321–364. For more recent syntheses and lead references to earlier synthetic work, see: (b) Back, T. G.; Baron, D. L.; Luo, W.; Nakajima, S. K., *J. Org. Chem.* 1997, 62, 1179–1182. (c) McMorris, T. C.; Chavez, R. G.; Patil, P. A. *J. Chem. Soc., Perkin Trans.* 1 1996, 295–301.
3. Cutler, H. G.; Yokota, T.; Adam, G., Eds. *Brassinosteroids: Chemistry, Bioactivity and Applications*; ACS Symposium Series 474, American Chemical Society: Washington, D.C., 1991.
4. Sakurai, A.; Yokota, T.; Clouse, S. D., Eds. *Brassinosteroids: Steroidal Plant Hormones;* Springer-Verlag: Tokyo, 1999.
5. Khripach, V. A.; Zhabinskii, V. N.; de Groot, A. E. *Brassinosteroids: A New Class of Plant Hormones*; Academic Press, San Diego, 1999.
6. Adam, G.; Porzel, A.; Schmidt, J.; Schneider, B.; Voigt, B. In *Studies in Natural Products Chemistry*; Atta-ur-Rahman, Ed., Elsevier: Amsterdam, 1996, Vol. 18; pp. 495–549.
7. Mandava, N. B. *Ann. Rev. Plant Physiol. and Plant Mol. Biol.* 1988, 39, 23.
8. Adam, G.; Marquardt, V., *Phytochemistry* 1986, 25, 1787.
9. Brosa, C. In *Biochemistry and Function of Sterols*; Parish, E. J.; Nes, W. D., Eds., CRC Press: Boca Raton, Fla., 1997; pp. 201–220.
10. Brosa, C.; Capdevila, J. M.; Zamora, I., *Tetrahedron* 1996, 52, 2435–2448.
11. Yokota, T.; Mori, K. In *Molecular Structure and Biological Activity of Steroids*; Bohl, M.; Duax, W. L. Eds., CRC Press: Boca Raton, Fla., 1992; pp. 317–340.
12. Takatsuto, S.; Yazawa, N.; Ikekawa, N.; Takematsu, T.; Takeuchi, Y.; Koguchi, M. *Phytochemistry* 1983, 22, 2437–2441.
13. Thompson, M. J.; Meudt, W. J.; Mandava, N. B.; Dutky, S. R.; Lusby, W. R.; Spaulding, D. W. *Steroids,* 1982, 39, 89–105.

14. Luo, W.; Janzen, L.; Pharis, R. P.; Back, T. G. *Phytochemistry* 1998, 49, 637–642.
15. Although some 5β-isomers have been reported to possess bioactivity (see ref. 10), contrary findings have also been reported: Seto, H.; Fujioka, S.; Koshino, H.; Suenaga, T.; Yoshida, S.; Watanabe, T.; Takatsuto, S. *Phytochemistry* 1999, 52, 815–818.
16. Baron, D. L.; Luo, W.; Janzen, L.; Pharis, R. P.; Back, T. G. *Phytochemistry* 1998, 49, 1849–1858.
17. (a) Back, T. G.; Janzen, L.; Nakajima, S. K., Pharis, R. P. *J. Org. Chem.* 1999, 64, 5494–5498. (b) Back, T. G.; Janzen, L.; Nakajima, S. K.; Pharis, R. P., *J. Org. Chem.* 2000, 65, 3047–3052. (c) Mori, K.; Takeuchi, T. *Liebigs Ann. Chem.* 1988, 815–818.
18. For other molecular modeling studies of brassinosteroids, see reference 10 and (a) Brosa, C.; Zamora, I.; Terricabras, E.; Soca, L.; Peracaula, R.; Rodríguez-Santamarta, C. *Lipids* 1997, 32, 1341–1347. (b) McMorris, T. C.; Patil, P. A.; Chavez, R. G.; Baker, M. E.; Clouse, S. D. *Phytochemistry* 1994, 36, 585–589. (c) Porzel, A.; Stoldt, M.; Drosihn, S.; Brandt, W.; Adam, G. *Proc. Plant Growth Reg. Soc. Am.* 1997, pp. 123–124. The conformation of 1 has also been investigated by other methods; by NMR spectroscopy: (d) Stoldt, M.; Porzel, A.; Adam, G.; Brandt, W. *Mag. Res. Chem.* 1997, 35, 629–636; by X-ray crystallography: see reference 1.
19. Sung, G. C. Y.; Janzen, L.; Pharis, R. P.; Back, T. G. *Phytochemistry*, in press
20. (a) Condon, M. E.; Cimarusti, C. M.; Fox, R.; Narayanan, V. L.; Reid, J.; Sundeen. J. E.; Hauck, F. P. *J. Med. Chem.* 1978, 21, 913. (b) Gutsche, C. D.; Peter, H. H. *Org. Synth.* 1957, 37, 80–82. (c) Kometani, T.; Watt, D. S.; Ji, T. *Tetrahedron Lett.* 1985, 26, 2043–2046.
21. (a) Sonogashira, K.; Tohda, Y.; Hagihara, N. *Tetrahedron Lett.* 1975, 4467–4470. (b) Sonogashira, K. In *Comprehensive Organic Synthesis*; Trost, B. M., Fleming, I. Eds., Pergamon Press: Oxford, 1991, Vol. 3; p. 521–561. (c) Tsuji, J. *Palladium Reagents and Catalysts*; Wiley: Chichester, 1995; pp. 168–178.
22. (a) Rowe, F. M.; Levin, E. *J. Chem. Soc.* 1920, 117, 1574–1579. (b) Holzapfel, C. W.; Koekemoer, J. M.; Van Dyk, M. S. S. Aft. *J. Chem.* 1986, 39, 158–161.
23. (a) Stille, J. K. *Angew. Chem., Int. Ed. Engl.* 1986, 25, 508–524. (b) Reference 21c, pp. 228–239.
24. Renaldo, A. F.; Labadie, J. W.; Stille, J. K. *Org. Synth.* 1988, 67, 86–87.
25. (a) Mash, E. A.; Nelson, K. A.; Van Deusen, S.; Hemperly, S. B. *Org. Synth.* 1990, 68, 92–103. (b) Khanapure, S. P.; Najafi, N.; Manna, S.; Yang, J. -J.; Rokach, J. *J. Org. Chem.* 1995, 60, 7548–7551. (c) Scharf, H. -D.; Plum, H.; Fleischhauer, J.; Schleker, W. *Chem. Ber.* 1979, 112, 862–882.
26. Johnson, W. S.; Bauer, V. J.; Margrave, J. L.; Frisch, M. A.; Dreger, L. H.; Hubbard, W. N. *J. Am. Chem. Soc.* 1961, 83, 606–614.
27. Hosten, N. G. C.; Tavernier, D.; Anteunis, M. J. O. *Bull. Soc. Chim. Belg.* 1985, 94, 183–186.
28. (a) Luijten, J. G. A.; Van Der Kerk, G. J. M. *Rec. Trav. Chim. Pays-Bas* 1964 83, 295–300. b) Luijten, J. G. A.; Janssen, M. J.; Van Der Kerk, G. J. M. *Rec. Trav. Chim. Pays-Bas* 1962 81, 202–205.
29. Henbest, H. B.; Smith, M.; Thomas, A. *J. Chem. Soc.* 1958, 3293–3298.
30. Takeno, K.; Pharis, R. P. *Plant and Cell Physiol.* 1982, 23, 1275–1281.
31. Sasse, J. M., in reference 3, pp. 158–166.

The disclosure of the above references are herein incorporated by reference in their entirety to the same extent as if the language of each individual reference were specifically and individually included herein.

What is claimed is:

1. A non-steroidal mimetic of a brassinosteroid having the formula:

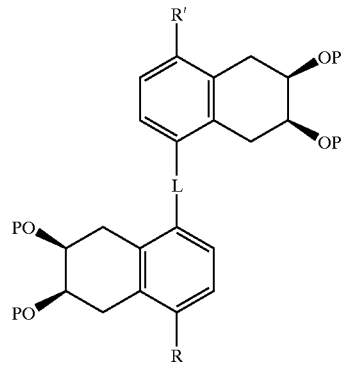

wherein:
(a) OP represents hydroxy or an ester from the group consisting of C1-C4 carboxylic acid esters, such that the hydroxy groups of each vicinal diol pair are cis and in a gauche relationship;
(b) R represents a polar functional group corresponding to the B-ring polar group of a brassinosteroid;
(c) R' represents hydrogen or hydroxy;
(d) L represents an acetylene linker or a trans-ethylene linker which joins the two bicyclic subunits such that each vicinal pair of hydroxyl groups and the polar group is substantially super imposable on the vicinal pairs and B-ring polar group of a brassinosteroid respectively.

2. The mimetic of claim 1 wherein R represents hydroxy.

3. The mimetic of claim 1 comprising a compound selected from the group consisting of:
(±)-1,2-bis[4,6α,7α-trihydroxy-5,6,7,8-tetrahydronaphthyl]ethyne (mimetic 3) and its meso isomers;
1-[4,6α,7α-trihydroxy-5,6,7,8-tetrahydronaphthyl]-2-[6α',7α'-dihydroxy-5',6',7',8'-tetrahydronaphthyl]ethyne (mimetic 4) as two diastereomeric (±) pairs;
(E)-(±)-1,2-bis[4,6α,7α-trihydroxy-5,6,7,8-tetrahydronaphthyl]ethene (mimetic 6) and its meso isomer; and
(E)-(±)-1,2-bis[trans-(4aα,8aβ)-4-oxo-6α,7α-dihydroxy-4a,5,6,7,8,8a-hexahydro-(3H)-naphthyl]ethene (mimetic 11) and its meso isomer;
or esters thereof, said esters selected from the group consisting of $C_1$-$C_4$ carboxylic acid esters.

4. A method for synthesizing mimetic 11 and its meso isomer which comprises:
a) preparation of (cis-4a,8a)-2,3,4a,5,8,8a-hexahydro-1,4-naphthalenedione by Diels-Alder cycloaddition of benzoquinone and 1,3-butadiene;
b) monoprotection of (cis-4a,8a)-2,3,4a,5,8,8a-hexahydro-1,4-naphthalenedione to produce (±)-4,4-(2,2-Dimethylpropylenedioxy)-2,3,4,4a,5,8,8a-hexahydro-1-naphthalenone;
c) cis-dihydroxylation to produce (±)-trans-(4aα,8aβ)-4,4(2,2-Dimethylpropylenedioxy)-6α,7α-dihydroxy-2,3,4,4a,5,6,7,8,8a-octahydro-1-naphthalenone; its trans-(4aα,8aβ)-6β,7β and cis-(4aα,8aα)-6α,7α isomers;

d) ketalization of the diol moiety of (±)-trans-(4aα,8aβ)-4,4-(2,2-dimethylpropylenedioxy)-6α,7α-dihydroxy-2,3,4,4a,5,6,7,8,8a-octahydro-1-naphthalenone and its trans-(4aα,8aβ) isomer to produce (±)-trans-(4aα,8aβ)-4,4-(2,2-dimethylpropylenedioxy)-6α,7α-(isopropylidenedioxy)-2,3,4,4a,5,6,7,8,8a-octahydro-1-naphthalenone;

e) ketalization of (±)-cis-(4aα,8α)-4,4-(2,2-dimethylpropylenedioxy)-6α,7α-dihydroxy-2,3,4,4a,5,6,7,8,8a-octahydro-1-naphthalenone, followed by quantitative base-catalyzed epimerization via the corresponding enolate, to produce (±)-trans-(4aα,8aβ)-4,4-(2,2-dimethylpropylenedioxy)-6α,7α-(isopropylidenedioxy)-2,3,4,4a,5,6,7,8,8a-octahydro-1-naphthalenone;

f) conversion of (±)-trans-(4aα,8aβ)-4,4-(2,2-dimethylpropylenedioxy)-6α,7α-(isopropylidenedioxy)-2,3,4,4a,5,6,7,8,8a-octahydro-1-naphthalenone into (±)-trans-(4aα,8aβ)-4,4-(2,2-dimethylpropylenedioxy)-6α,7α-(isopropylidenedioxy)-1-trifloxy-4a,5,6,7,8,8a-hexahydro-(3H)-naphthalene; and g) Stille coupling with trans-bis(tri-n-butylstannyl)ethylene and deprotection.

5. The method for synthesizing mimetic 3 as a mixture of its corresponding meso and (±) isomers, which comprises:

(a) synthesis of tetrahydronapthalene from α-naphthol;

(b) iodination in the para position with chloramine T and sodium iodide to generate (±)-4-iodo-6α,7α-(isopropylidenedioxy)-5,6,7,8-tetrahydro-1-naphthol;

(c) Sonogashira coupling of (±)-4-iodo-6α,7α-(isopropylidenedioxy)-5,6,7,8-tetrahydro-1-naphthol with trimethylsilylacetylene to generate (±)-4-ethynyl-6α,7α-(isopropylidenedioxy)-5,6,7,8-tetrahydro-1-naphthol; and (d) dihydroxylation and Sonogashira coupling of (±)-4-iodo-6α,7α-(isopropylidenedioxy)-5,6,7,8-tetrahydro-1-naphthol with (±)-4-ethynyl-6α,7α-(isopropylidenedioxy)-5,6,7,8-tetrahydro-1-naphthol, to produce (±)-1,2-bis[4-hydroxy-6α,7α-(isopropylidenedioxy)-5,6,7,8-tetrahydro-naphthyl]ethyne and its meso isomer; and (e) deprotection of (±)-1,2-bis[4-hydroxy-6α,7α-(isopropylidenedioxy)-5,6,7,8-tetrahydro-naphthyl]ethyne.

6. A method for synthesizing mimetic 4 as two diastereomeric (±) pairs which comprises:

(a) synthesis of tetrahydonaphthalene from α-naphthol;

(b) iodination in the para position with chloramine T and sodium iodide to generate (±)-4-iodo-6α,7α-(isopropylidenedioxy)-5,6,7,8-tetrahydro-1-naphthol;

(c) protection of 14 as the t-butyldimethylsilyl ether 20; -and (d) Sonogashira coupling of (±)-1-t-butyldimethylsilyloxy-4-iodo-6α,7α-(isopropylidenedioxy)-5,6,7,8-tetrahydronaphthalene with (±)-1-ethynyl-5,6,7,8-tetrahydro-6α,7α-naphthalenediol, followed by removal of protecting groups.

7. A method for synthesizing mimetic 6 and its meso isomer which comprises:

a) Stille coupling of (±)-1-t-butyldimethylsilyloxy-4-iodo-6α,7α-(isopropylidenedioxy)-5,6,7,8-tetrahydronaphthalene with trans-bis(tri-n-butylstannyl)ethylene to produce (E)-(±)-1,2-bis[6α,7α-(isopropylidenedioxy)-4-t-butyl dimethylsilyloxy-5,6,7,8-tetrahydronaphthyl]ethene and its meso isomer; and b) deprotection of (E)-(±)-1,2-Bis[6α,7α-(isopropylidenedioxy)-4-t-butyldimethylsilyloxy-5,6,7,8-tetrahydronaphthyl]ethene.

8. A composition for promoting plant growth comprising:

a) a mimetic of claim 4 in a suitable delivery vehicle; and b) a plant growth regulator from the group consisting of auxins, cytokinins, or giberellins.

9. The composition of claim 8 wherein the plant growth regulator is an auxin, said auxin comprising indole-3-acetic acid or naphthaleneacetic acid.

10. A method of promoting plant growth by applying to the plant an effective amount of a mimetic of claim 4 in a suitable delivery vehicle, in conjunction with a plant growth regulator wherein the plant growth-regulator is an auxin, a cytokinin or a gibberellin.

11. The method of claim 10 wherein the plant growth regulator is an auxin and comprises indole-3-acetic acid or naphthaleneacetic acid.

12. A method of promoting a desired tissue morphology and/or physiological state in a higher plant, wherein said desired tissue morphology or physiological state is selected from at least one of: shoot growth, grain, seed or fruit yield enhancement, root (radicle) growth retardation, improved fruit set and fruit quality or other desired tissue morphology or physiological state that is promoted by a brassinosteroid, said method comprising the step of applying an effective amount of a mimetic of claim 4 in a suitable delivery vehicle, in conjunction with a plant growth regulator and an appropriate formulating agent, wherein the plant growth regulator is an auxin, a cytokinin or a gibberellin.

13. The method of claim 12 wherein the plant growth regulator is an auxin.

14. The method of claim 13 wherein the auxin comprises indole-3-acetic acid or naphthaleneacetic acid.

* * * * *